US007592427B2

(12) United States Patent
Sivakumar et al.

(10) Patent No.: US 7,592,427 B2
(45) Date of Patent: Sep. 22, 2009

(54) ANTIBODIES TO IL-21 RECEPTOR

(75) Inventors: Pallavur V. Sivakumar, Seattle, WA (US); Stephen R. Jaspers, Edmonds, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/564,001

(22) Filed: Nov. 28, 2006

(65) Prior Publication Data

US 2007/0128189 A1 Jun. 7, 2007

Related U.S. Application Data

(60) Provisional application No. 60/739,995, filed on Nov. 28, 2005.

(51) Int. Cl.
*C12P 21/08* (2006.01)
(52) U.S. Cl. ............... 530/388.1; 530/387.3; 530/809; 530/350; 424/133.1; 435/70.2; 435/70.21
(58) Field of Classification Search ................... None
See application file for complete search history.

(56) References Cited

U.S. PATENT DOCUMENTS

| | | | |
|---|---|---|---|
| 5,510,259 A * | 4/1996 | Sugamura et al. | ............ 435/356 |
| 6,057,128 A | 5/2000 | Donaldson et al. | |
| 6,576,744 B1 | 6/2003 | Presnell et al. | |
| 6,692,924 B2 | 9/2003 | Novak et al. | |
| 6,777,539 B2 | 8/2004 | Sprecher et al. | |
| 6,803,451 B2 | 10/2004 | Presnell et al. | |
| 7,189,695 B2 | 3/2007 | Sprecher et al. | |
| 2004/0016010 A1 | 1/2004 | Kasaian et al. | |
| 2004/0057902 A1 | 3/2004 | Gold et al. | |
| 2004/0136954 A1 | 7/2004 | Grusby et al. | |
| 2004/0204562 A1 | 10/2004 | Presnell et al. | |
| 2004/0265960 A1 | 12/2004 | Young et al. | |
| 2005/0019343 A1 | 1/2005 | Schenk | |
| 2005/0048577 A1 | 3/2005 | Novak et al. | |
| 2006/0024268 A1 | 2/2006 | Kasaian et al. | |
| 2006/0039902 A1 | 2/2006 | Young et al. | |
| 2006/0159655 A1 | 7/2006 | Collins et al. | |
| 2007/0111941 A1 | 5/2007 | Presnell et al. | |
| 2007/0122413 A1 | 5/2007 | Sivakimar et al. | |
| 2007/0172917 A1 | 7/2007 | Presnell et al. | |
| 2007/0178096 A1 | 8/2007 | Presnell et al. | |
| 2007/0178488 A1 | 8/2007 | Novak et al. | |
| 2007/0212788 A1 | 9/2007 | Novak et al. | |
| 2007/0224118 A1 | 9/2007 | Sprecher et al. | |
| 2008/0032333 A1 | 2/2008 | Sprecher et al. | |

FOREIGN PATENT DOCUMENTS

| | | |
|---|---|---|
| JP | 2005306757 | 11/2005 |
| WO | 0177171 | 4/2001 |
| WO | 03087320 | 4/2003 |
| WO | 2004/083249 | 9/2004 |
| WO | 2006057027 | 6/2006 |

OTHER PUBLICATIONS

U.S. Appl. No. 11/538,359, filed Oct. 3, 2006.
U.S. Appl. No. 11/538,319, filed Oct. 3, 2006.
U.S. Appl. No. 11/538,331, filed Oct. 3, 2006.
Brandt et al., "Generation of Antagonists by Amino Acid Replacement in the D-Helix of Human IL-21," *J. Leukocyte Biol.* S2001, abstr. 119, 2001, Publisher Not Available.
Caruso et al., "A Functional Role for Interleukin-21 in Promoting the Synthesis of the T-Cell Chemoattractant, MIP-3α, by Gut Epithelial Cells," *Gastroenterology* 132:166-175, 2007.
Kasaian et al., "IL21 blocks IL15-induced NK cell expansion and enhances IFNγ production," *J. Leukocyte Biol.* S2001, abstr. 78, 2001, Publisher Not Available.
Olosz et al., "Structural Basis for Binding Multiple Ligands by the Common Cytokine Receptor γ-Chain," *J. Biol. Chem.* 277(14):12047-12052, 2002.
Suto et al., "Interleukin 21 prevents antigen-induced IgE production by inhibiting germ line Cε transcription of IL-4-stimulated B cells," *Blood* 100(13):4565-4573, 2002.
Zhang et al., "Human IL-21 and IL-4 bind to partially overlapping epitopes of common γ-chain," *Biochemical and Biophysical Research Communications* 300:291-296, 2003.
Hecker et al., "Novel genetic variation of human interleukin-21 receptor is associated with elevated IgE levels, in females," *Genes and Immunity* 4:228-233, 2003.
Cohen et al., "Increased expression of CD132 and multiple IL-2 family receptors in psoriasis vulgaris," *J. Investigative Dermatol*, abstr. 0115, 2003, Publisher Not Available.
Distler et al., "Inflammation-independent Overexpression of JL-21 Receptor mRNA in Keratinocytes from patients with Systemic Sclerosis," *American College of Rheumatology Abstract Supplement*, abstr. 848, 2003, Publisher Not Available.
Brandt et al., "Interleukin-21 Inhibits Dendritic Cell-Mediated T Cell Activation and Induction of Contact Hypersensitivity In Vivo," *J. Invest. Dermatol.* 121(6):1379-82, 2003.
Brandt et al., "Interleukin-21 inhibits dendritic cell activation and maturation," *Blood* 102(12):4090-4098, 2003.
Distler, "Overexpression of IL-21 Receptor mRNA in the Epidermis of Patients with Systemic Sclerosis: Lessions from the SCID Mouse Transplantation Model," *Annals of the Rheumatic Diseases* 63(S1):107, OP0158, 2004.
Alexopoulos et al., "Tolerance Induction Using IL-21 Antagonizing Fusion Protein," *Experimental Tolerance Induction 1*, Abstract #101, 2004.

(Continued)

*Primary Examiner*—Dong Jiang
(74) *Attorney, Agent, or Firm*—Deborah A. Sawislak; Nicholas V. Sherbina

(57) ABSTRACT

Monoclonal antibodies to the IL-21 receptor and multimeric complexes comprising the IL-21 receptor; including monoclonal antibodies to the heterodimeric receptor, IL-21/IL-2Rγ; have been prepared. The invention also describes a method of producing said antibodies. And, the invention also describes a method of treatment comprising using said antibodies to suppress an immune response.

5 Claims, No Drawings

OTHER PUBLICATIONS

O'Shea et al., "A New Modality for Immunosuppression: Targeting the JAK/STAT Pathway," *Nature Reviews* 3:555-564, 2004.

O'Shea et al., "Jak3 and the pathogenesis of severe combined immunodeficiency," *Molecular Immunology* 41:727-737, 2004.

Wood et al., "IL-21 effects on human IgE production in response to IL-4 or IL-13," *Cellular Immunology* 231:133-145, 2004.

Habib et al., "The Common Gamma Chain is a Required Signaling Component of the IL-21 Receptor and Supports IL-21 Induced Cell Proliferation via JAK3," *Biochemistry* 41(27): Jul. 9, 2002.

Stauber et al., "Crystal structure of the IL-2 signaling complex: Paradigm for a deterotrimeric cytokine receptor," PNAS 103(8): 2788-2793, 2006.

* cited by examiner

US 7,592,427 B2

ANTIBODIES TO IL-21 RECEPTOR

REFERENCE TO RELATED APPLICATIONS

This application claims the benefit of U.S. Provisional Application Ser. No. 60/739,995, filed Nov. 28, 2005, which is herein incorporated by reference.

BACKGROUND OF THE INVENTION

Cytokines generally stimulate proliferation or differentiation of cells of the hematopoietic lineage or participate in the immune and inflammatory response mechanisms of the body. The interleukins are a family of cytokines that mediate immunological responses. Central to an immune response is the T cell, which produces many cytokines and provides adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic 200 residue extracellular domain.

The immune system is the body's primary defense against diseases caused by pathogens, namely bacteria, viruses, fungi etc, as well as against diseases caused by abnormal growth of the body's own cells and tissues (i.e. cancerous tumors). Normally, the immune system is able to distinguish between the body's normal cells or "self" and foreign pathogens or abnormal cells or "non-self". The processes by which the immune system refrains from reacting to one's own body is called tolerance. Sometimes, the immune system loses the ability to recognize "self" as normal and the subsequent response directed against the tissue or cells, results in loss of tolerance, a state of autoimmunity. The pathologies resulting from autoimmunity often have serious clinical consequences and are one of the major health problems in the world, especially in developed nations.

The demonstrated in vivo activity of these cytokines and their receptors illustrate the enormous clinical potential of, and need for cytokine antagonists. The present invention addresses this need by providing a new cytokine antagonist or binding partner, an antibody to a hematopoietic cytokine receptor, as well as related compositions and methods.

The present invention provides such antibodies for these and other uses that should be apparent to those skilled in the art from the teachings herein.

BRIEF SUMMARY OF THE INVENTION

Within one aspect, the present invention provides antibodies, monoclonal antibodies, and antibody fragments that specifically bind to a receptor or a multimeric or heterodimeric receptor complex comprising IL-21R, the IL-21 receptor ("SEQ ID NO:2" or "zalpha11"). Exemplary antibodies include neutralizing antibodies, and may be murine monoclonal antibodies, humanized antibodies derived from murine monoclonal antibodies, and human monoclonal antibodies. Illustrative antibody fragments include F(ab')2, F(ab)2, Fab', Fab, Fv, scFv, and minimal recognition units. Neutralizing antibodies preferably bind IL-21 receptor or a receptor complex comprising IL-21 receptor such that IL-21 binding to the IL-21 receptor or receptor complex is blocked, inhibited, reduced, antagonized or neutralized.

Within another aspect, the present invention also provides anti-idiotype antibodies, or anti-idiotype antibody fragments, that specifically bind an antibody or antibody fragment that specifically binds a polypeptide comprising the amino acid sequence of SEQ ID NO:2 or a fragment thereof. An exemplary anti-idiotype antibody binds with an antibody that specifically binds a heterodimeric receptor consisting of SEQ ID NO:2 and SEQ ID NO:4.

In another aspect, the present invention provides a monoclonal antibody that binds to an antigen receptor complex selected from the group consisting of (a) a homodimeric receptor complex comprising SEQ ID NO:2; (b) a heterodimeric or multimeric receptor complex comprising SEQ ID NO:2, and a Class I cytokine receptor polypeptide; (c) a heterodimeric or multimeric receptor complex comprising SEQ ID NO:2, and an IL-2Rγ receptor polypeptide comprising SEQ ID NO:4.

In another aspect, the present invention provides a monoclonal antibody that binds to an epitope of an antigen receptor complex selected from the group consisting of (a) a homodimeric receptor complex comprising SEQ ID NO:2; (b) a heterodimeric or multimeric receptor complex comprising SEQ ID NO:2, and a Class I cytokine receptor polypeptide; (c) a heterodimeric or multimeric receptor complex comprising SEQ ID NO:2, and an IL-2Rγ receptor polypeptide comprising SEQ ID NO:4.

Within another aspect, the present invention provides a method of producing an antibody to a receptor polypeptide comprising inoculating an animal with a receptor polypeptide complex selected from the group consisting of (a) a polypeptide comprising a homodimeric receptor complex comprising SEQ ID NO:2; (b) a polypeptide comprising a receptor heterodimeric or multimeric receptor complex comprising SEQ ID NO:2; (c) a polypeptide comprising a receptor heterodimeric or multimeric receptor complex comprising SEQ ID NO:2, and further comprising a Class I cytokine receptor polypeptide; and (d) a polypeptide comprising a receptor heterodimeric or multimeric receptor complex comprising SEQ ID NO:2, and further comprising an IL-2Rγ receptor polypeptide (SEQ ID NO:4); and wherein the polypeptide complex elicits an immune response in the animal to produce the antibody; and isolating the antibody from the animal.

Within another aspect, the present invention provides an antibody produced by the method as disclosed above, which specifically binds to a homodimeric, heterodimeric or multimeric receptor complex comprising a receptor polypeptide comprising SEQ ID NO:2. In one embodiment the antibody disclosed above is a monoclonal antibody.

Within another aspect, the present invention provides hybridomas that produce an antibody which specifically binds to a homodimeric, heterodimeric or multimeric receptor complex as disclosed above.

Within another aspect, the present invention provides antagonists to the binding of IL-21 receptor, or a complex comprising IL-21 receptor, to the IL-21 ligand, such as anti- IL-21R or anti-IL-21 receptor/IL-2Rγ antibodies, which are useful in therapeutic treatment of inflammatory diseases. For example, anti-IL-21 receptor or anti-IL-21 receptor/IL-2Rγ antibodies are useful in the treatment of autoimmune disease is selected from the group consisting of pancreatitis, type I diabetes (IDDM), Graves Disease, inflammatory bowel disease (IBD), Crohn's Disease, multiple sclerosis, rheumatoid arthritis, diverticulosis, systemic lupus erythematosus, psoriasis, ankylosing spondylitis, scleroderma, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versous host disease, host versus graft disease, atopic dermatitis, ulcerative colitis, and asthma.

These and other aspects of the invention will become evident upon reference to the following detailed description of the invention.

The following definitions are provided to facilitate understanding of the inventions described herein.

The term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "variant" anti-IL-21 receptor antibody, refers herein to a molecule which differs in amino acid sequence from a "parent" anti-IL-21 receptor antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-21 receptor and preferably has properties which are superior to those of the parent antibody. For example, the variant may have a stronger binding affinity, enhanced ability to inhibit IL-21 receptor-induced stimulation of immune cells. To analyze such properties, one should compare a Fab form of the variant to a Fab form of the parent antibody or a full length form of the variant to a full length form of the parent antibody, for example, since it has been found that the format of the anti-IL-21 receptor antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The term "parent antibody" as used herein refers to an antibody which is encoded by an amino acid sequence used for the preparation of the variant. Preferably, the parent antibody has a human framework region and, if present, has human antibody constant region(s). For example, the parent antibody may be a humanized or human antibody.

The term "receptor" is used herein to denote a cell-associated protein, or a polypeptide subunit of such a protein, that binds to a bioactive molecule (the "ligand") and mediates the effect of the ligand on the cell. The term "receptor polypeptide" is used to denote complete receptor polypeptide chains and portions thereof, including isolated functional domains (e.g., ligand-binding domains).

The term "agonist" refers to any compound including a protein, polypeptide, peptide, antibody, antibody fragment, large molecule, or small molecule (less than 10 kD), that increases the activity, activation or function of another molecule. For example, IL-21 receptor agonists cause stimulation of cells comprising: NK cells, dendritict cells, T cell subsets, and B cell subsets.

The term "antagonist" refers to any compound including a protein, polypeptide, peptide, antibody, antibody fragment, large molecule, or small molecule (less than 10 kD), that decreases the activity, activation or function of another molecule. By example, IL-21 receptor antagonists cause decreased immune function of cells comprising: NK cells, dendritic cells, T cell subsets, and B cell subsets.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, Clin. Exp. Immunol. 79:315-321 (1990); Kostelny et al., J. Immunol. 148:1547-1553 (1992).

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

The term "effective neutralizing titer" as used herein refers to the amount of antibody which corresponds to the amount present in the serum of animals (human or cotton rat) that has been shown to be either clinically efficacious (in humans) or to reduce virus by 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu) of RSV.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-21R epitope" as used herein refers to a portion of an IL-21R polypeptide having antigenic or immunogenic activity in an animal, preferably in a mammal, and most preferably in a mouse or a human. An epitope having immunogenic activity is a portion of an IL-21R polypeptide that elicits an antibody response in an animal. An epitope having antigenic activity is a portion of an IL-21R polypeptide to which an antibody immunospecifically binds as determined by any method well known in the art, for example, by immunoassays. Antigenic epitopes need not necessarily be immunogenic.

The term "epitope tagged" when used herein refers to the anti-IL-21 antibody fused to an "epitope tag". The epitope tag polypeptide has enough residues to provide an epitope against which an antibody can be made, yet is short enough such that it does not interfere with activity of the IL-21 antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereto (Evan et al., *Mol. Cell. Biol.* 5(12): 3610-3616(1985)); and the Herpes Simplex virus glycoprotein D (gD) tag and its antibody (Paborsky et al., *Protein Engineering* 3(6):547-553(1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues of the amino acid sequence of an IL-21 polypeptide or an antibody that immunospecifically binds to an IL-21 polypeptide.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes and antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies (as described above and in detail in: Lanzavecchia et al., *Eur. J. Immunol.* 17, 105 (1987)) and in single chains (e.g., Huston et al., *Proc. Natl. Acad. Sci. U.S.A.*, 85 5879-5883 (1988) and Bird et al., *Science*, 242:423-426 (1988), which are incorporated herein by reference). (See, generally, Hood et al., "Immunology", Benjamin, N.Y., 2nd ed. (1984), and Hunkapiller and Hood, *Nature*, 323:15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The term "linear antibodies" refers to the antibodies described in Zapata et al. *Protein Eng.* 8(10):1057-1062 (1995). Briefly, these antibodies comprise a pair of tandem Fd segments ($V_{H1}$-$C_{H1}$-$V_H$-$C_{H1}$) which form a pair of antigen binding regions. Linear antibodies can be bispecific or monospecific.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof. Preferably, an immunologically functional immunoglobulin fragment of the invention binds specifically to IL-21.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The present invention also includes genetically altered antibodies that are functionally equivalent to the above-described antibodies. Modified antibodies providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Antibodies of the present invention can be can be modified post-translationally (e.g., acetylation, and phosphorylation) or can be modified synthetically (e.g., the attachment of a labeling group).

The genetically altered antibodies also include chimeric antibodies that are derived from the anti-IL-21 receptor antibodies. Preferably, the chimeric antibodies comprise a variable region derived from a mouse or rat and a constant region derived from a human so that the chimeric antibody has a longer half-life and is less immunogenic when administered to a human subject. The method of making chimeric antibodies is known in the art. The variable regions of these antibodies can be connected with a constant region of a human IgG to form the desired chimeric antibody.

Preferably, the genetically altered anti-IL-21 receptor antibodies used in the present invention include humanized version of the antibodies described herein. In certain embodiments, the humanized antibody comprising CDRs of a mouse donor immunoglobulin and heavy chain and light chain frameworks of a human acceptor immunoglobulin. The method of making humanized antibody is disclosed in U.S. Pat. Nos. 5,301,101; 5,585,089; 5,693,762; and 6,180,370 (each of which is incorporated by reference in its entirety). The CDRs of these antibodies can then be grafted to any selected human frameworks, which are known in the art, to generate the desired humanized antibody.

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, or by size in contiguous amino acid residues. Antibodies of the present invention may also be described or specified in terms of their cross-reactivity. Antibodies that do not bind any other analog, ortholog, or homolog of a polypeptide of the present invention are included.

Epitope binning refers to the use of competitive binding assays to identify pairs of antibodies that are, or are not, capable of binding IL-21 receptor proteins or IL-21 receptor protein complexes simultaneously thereby identifying antibodies that bind to the same, or overlapping epitopes on the proteins. Families of antibodies (or bins) having the same binding specificity can then be used to define specific epitopes on the IL-21 receptor protein or on the IL-21 receptor protein complex. Epitope binning experiments provide evidence that antigenically distinct epitopes are present. However, by themselves, they do not identify, or "map" the epitope to a specific amino acid sequence or location on the IL-21 receptor protein or IL-21 receptor protein complex molecules.

Competition for binding can be evaluated for any pair of antibodies or fragments. For example, using the appropriate detection reagents, the binding specificity of antibodies or binding fragments from any species/source can be compared to the binding specificity of the monoclonal antibodies disclosed herein. Epitope binning can be performed with "isolated antibodies" or with cell culture supernatants. Frequently binning is performed with first round clonal supernatants to guide the choice of clones to be developed further. The antibodies to be compared should have substantially homogeneous antigen binding domains. In the case of "bispecific" or "bifunctional" antibodies the binding specificity of the two different binding sites need to be evaluated or binned independently.

The present invention features both receptor-specific antibodies and ligand-specific antibodies. In addition to competitive binding of antibodies, epitope binning can also be used to identify antibodies to either a receptor or a ligand that competitively interfere with the binning of a ligand and its receptor. Frequently, favorable properties, of a family (or bin) of antibodies can correlated with a binding to a specific epitope defined by the epitope bin.

Competitive binding experiments do not directly measure the binding affinity, however the antibodies to be tested must bind sufficiently strongly to act as competitors. Generally experimental conditions are designed to minimize the effects of differences in binding affinity.

Anti-IL-21 receptor or receptor complex antibodies may also be useful in diagnostic assays for IL-21 rexeptor or receptor complex proteins, e.g., detecting their expression in specific cells, tissues, or serum. Antibodies assigned to different bins and capable of binding to different immunogenic portions, or epitopes of the IL-21 receptor or receptor complex may be used as the reagents for sandwich assays. In a sandwich assay, the test sample analyte is captured by a first antibody which is immobilized on a solid support, and thereafter detected by a second antibody that also binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the instant invention may be assayed for specific binding by any method known in the art. Many different competitive binding assay format(s) can be used for epitope binning. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York). Exemplary immunoassays are described briefly below (but are not intended by way of limitation). Additionally, a routine cross-blocking assay such as that described in Antibodies, A Laboratory Manual, Cold Spring Harbor Laboratory, Ed Harlow and David Lane (1988), can be performed.

The Biacore is only one of a variety of assay formats that are routinely used to epitope bin panels of monoclonal antibodies. Many references (e.g. The Epitope Mapping Protocols, Methods in Molecular Biology, Volume 6.6 Glenn E. Morris ed.) describe alternative methods that could be used to bin antibodies and would be expected to provide identical information regarding the binding specificity of the antibodies to the IL-21 receptor or receptor complex proteins. When using the Biacore system, epitope binning experiments are performed with native antigen. Epitope binning studies can be performed on a Biacore1000® system (Biacore, Uppsalla Sweden). BIAlogue® v. 1.2 software can be used for programming run methods. For the example of using the Biacore to bin mouse monoclonal antibodies raised against IL-21, polyclonal goat anti-Mouse IgG Fc antibody (Jackson ImmunoResearch Laboratories, West Grove, Pa.) can be covalently immobilized to a Biacore® CM5 sensor chip and used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, the IL-21 receptor or receptor complex protein is injected and allowed to specifically bind to the captured primary monoclonal antibody. The Biacore instrument measures the mass of protein bound to the sensor chip, and the binding of both the primary antibody and IL-21 receptor or receptor complex antigen can be verified for each cycle. Following the binding of the primary antibody and antigen to the chip, soluble secondary antibody is injected and allowed to bind to the pre-bound antigen. If the secondary monoclonal antibody is capable of binding the IL-21 receptor or receptor complex antigen simultaneously with the primary monoclonal antibody, its binding is detected by the Biacore. If, however, the secondary monoclonal antibody is not capable of binding the IL-21 receptor or receptor complex antigen simultaneously with the primary monoclonal antibody, no additional binding is detected. Each monoclonal antibody is tested against itself as a negative control to establish the level of the background (no-binding) signal.

A label-free competitive ELISA format (LFC-ELISA) can also be used to bin antibodies. This method is described by Nagata et al., *J. Immuno Methods* 292:141-155, 2004. This method for epitope binning utilizes biotinylated IL-21 receptor or receptor complex. For the example of binning mouse monoclonal antibodies raised against IL-21 receptor or receptor complex, microtiter plates are coated at 100 µL/well with 1 µg/mL of a goat anti-mouse IgG Fc-γ specific antibody (Jackson ImmunoResearch) diluted in ELISA B (PBS, 0.1% Tween 20, 1% BSA). After binding of this coating antibody for 3 hours at ambient temperature, each mAb-containing conditioned media is diluted in ELISA B to yield an approximate mAb concentration of 0.5 μg/mL and allowed to bind to the goat anti-mouse IgG coated plates overnight at 4° C. (mAb#1). In parallel, a second set of conditioned medias (mAb#2) are diluted in polystyrene test tubes to approximately 0.5 μg/mL mAb in ELISA B, mixed with 50 ng/mL biotinylated IL-21 receptor or receptor complex antigen, and incubated overnight at 4° C. After incubation of mAb#1 with the coating antibody, the plates are blocked with an unrelated antibody to saturate unoccupied binding sites on the plate. The mAb#2-biotin-IL-21 mixtures are added to the plate and allowed to bind. As a control for (non-competition) in the assay, 50 ng/mL biotinylated IL-21 receptor or receptor complex is added directly (without pre-incubation with mAb#2) to wells containing immobilized mAb#1. After incubation with the biotinylated IL-21 receptor or receptor complex mAb#2 complex, streptavidin-HRP (Pierce, Rockford, Ill.) is added to the plate at 0.5 μg/mL. The plates are developed with TMB substrate (BioFX Laboratories, Owings Mills, Md.), and the absorbance of the individual wells at 450 nm is measured with a plate reader (Molecular Devices Spectra-Max®340, Sunnyvale, Calif.). If mAb#1 binds to a different epitope from mAb#2, the biotin-IL-21 receptor or receptor complex mAb#2 complex will bind to the plate resulting in a high absorbance reading. If mAb#1 binds to the same epitope as mAb#2, the biotin-IL-21 receptor or receptor complex MAb#2 complex will not bind to the plate resulting in a low absorbance reading.

Antibodies of the present invention act as antagonists of IL-21 receptor or receptor complex. For example, the present invention includes antibodies which disrupt IL-21 receptor or receptor complex's receptor/ligand interactions either partially or fully. The invention features receptor-specific antibodies, and the invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex. Also included are receptor-specific antibodies that do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein.

DETAILED DESCRIPTION OF INVENTION

Production of Anti-IL-21R Antibodies

The IL-21 receptor or the IL-21 receptor heterodimeric polypeptide, such as an IL-21 receptor/IL-2Rγ polypeptide, can be used to prepare antibodies that bind to epitopes, peptides, or polypeptides contained within the antigen. Particularly useful anti-IL-21R antibodies "bind specifically" with IL-21R. Antibodies are considered to be specifically binding if the antibodies exhibit at least one of the following two properties: (1) they exhibit a threshold level of binding activity, and (2) they do not significantly cross-react with related polypeptide molecules.

With regard to the first characteristic, a threshold level of binding is determined if anti-IL-21R antibodies or anti-IL-21R heterodimeric antibodies, such as ani-IL-21R/IL-2Rγ antibodies, bind to IL-21R or IL-21R heterodimeric polypeptide, such as IL-21R/IL-2Rγ polypeptide, peptide or epitope with an affinity at least 10-fold greater than the binding affinity to control polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

With regard to the second characteristic, antibodies do not significantly cross-react with related polypeptide molecules if, for example, they can detect IL-21R or IL-21R heterodimeric polypeptide, such as IL-21R/IL-21Rγ polypeptide, but not other presently known related polypeptides using a standard Western blot analysis. Examples of known related polypeptides include those disclosed in the prior art, such as known orthologs, and paralogs, and similar known members of a protein family. Screening can also be done using non-human IL-21 receptor or IL-21 receptor heterodimeric polypeptide, such as IL-21 receptor/IL-2Rγ, and IL-21 receptor or IL-21 receptor heterodimeric polypeptide, such as IL-21 receptor/IL-2Rγ mutant polypeptides. Moreover, antibodies can be "screened against" known related polypeptides, to isolate a population that specifically binds to the IL-21 receptor or IL-21 receptor heterodimeric polypeptide, such as IL-21 receptor/IL-2Rγ polypeptides. For example, antibodies raised to IL-21 receptor or IL-21 receptor heterodimeric polypeptide, such as IL-21 receptor/IL-2Rγ are adsorbed to related polypeptides adhered to insoluble matrix; antibodies specific to IL-21 receptor or IL-21 receptor heterodimeric polypeptide, such as IL-21 receptor/IL-2Rγ will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), *Academic Press Ltd.*, 1996; Benjamin et al., *Ann. Rev. Immunol.* 2: 67-101, 1984. Specifically binding anti-IL-21 receptor or anti-IL-21 receptor heterodimeric polypeptide, such as anti-IL-21 receptor/IL-2Rγ antibodies can be detected by a number of methods in the art, and disclosed below.

Anti-IL-21R antibodies and antibodies to an antigen comprising IL-21R, such as the heterodimeric polypeptide IL-21R/IL-2Rγ, can be produced using antigenic peptides and polypeptides such as IL-21R or an IL-21R heterodimeric polypeptide like IL-21R/IL-2Rγ. This is done by using IL-21R or an IL-21R heterodimeric polypeptide like IL-21R/IL-2Rγ as an antigen (immunogen) to inoculate an animal and to elicit an immune response from that animal. One of skill in the art would recognize that antigenic, epitope-bearing polypeptides contain a sequence of at least 6, preferably at least 9, and more preferably at least 15 to about 30 contiguous amino acid residues of IL-21R or the IL-21R heterodimeric polylepeptide, such as IL-21R/IL-2Rγ polypeptides (e.g., SEQ ID NO:2, SEQ ID NO:4; SEQ ID NO:10). Polypeptides comprising a larger portion of an IL-21 receptor or IL-21 receptor heterodimeric polypeptide, such as IL-21 receptor/IL-2Rγ polypeptides i.e., from 30 to 100 residues up to the entire length of the amino acid sequence are included. Antigens or immunogenic epitopes can also include attached tags, adjuvants and carriers, as described herein. Suitable antigens include the IL-21 receptor polypeptide encoded by SEQ ID NO:2 from amino acid number 20 (Cys) to amino acid number 237 (His) (SEQ ID NO:6), or a contiguous 9 to 218 AA amino acid fragment thereof. Preferred peptides to use as antigens are the cytokine binding domain, disclosed herein, and IL-21 receptor hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored. For example, IL-21 receptor hydrophilic peptides include peptides comprising amino acid sequences selected from the group consisting of: (1) amino acid number 51 (Trp) to amino acid number 61 (Glu) of SEQ ID NO:2; (2) amino acid number 136 (Ile) to amino acid number 143 (Glu) of SEQ ID NO:2; (3) amino acid number 187 (Pro) to amino acid number 195 (Ser) of SEQ ID NO:2; and (4) amino acid number 223 (Phe) to amino acid number 232 (Glu) of SEQ ID NO:2. The corresponding hydrophilic regions in reference to SEQ ID NO:2 can be made with cross-reference to the above amino acid residues of SEQ ID NO:2. Moreover, antigenic epitope-bearing polypeptides as predicted by a Jameson-Wolf plot, e.g., using DNASTAR Protean program (DNASTAR, Inc., Madison, Wis.) are suitable antigens. In addition, conserved motifs, and variable regions between conserved motifs of IL-21 receptor are suitable antigens. Suitable antigens also include the IL-21 receptor polypeptides disclosed above in combination with another class I cytokine extracellular domain, such as those that form IL-21 receptor heterodimeric polypeptides, such as IL-21 receptor/IL-2Rγ. Moreover, corresponding regions of the mouse IL-21 receptor polypeptide (residues 20 (Cys) to 237 (His) (SEQ ID NO:8) can be used to generate antibodies against the mouse IL-21 receptor. In addition Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

Polyclonal antibodies to a polypeptide comprising recombinant IL-21R protein or to a polypeptide comprising IL-21R that is isolated from natural sources can be prepared using methods well-known to those of skill in the art. See, for example, Green et al., "Production of Polyclonal Antisera," in Immunochemical Protocols (Manson, ed.), pages 1-5 (Humana Press 1992), and Williams et al., "Expression of foreign proteins in *E. coli* using plasmid vectors and purification of specific polyclonal antibodies," in DNA Cloning 2: Expression Systems, 2nd Edition, Glover et al. (eds.), page 15 (Oxford University Press 1995). The immunogenicity of an IL-21R polypeptide can be increased through the use of an adjuvant, such as alum (aluminum hydroxide) or Freund's complete or incomplete adjuvant. Polypeptides useful for immunization also include fusion polypeptides, such as fusions of IL-21R or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-IL-21R antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-IL-21R antibodies can be generated. Rodent mono-clonal antibodies to specific antigens may be obtained by methods known to those skilled in the art (see, for example, Kohler et al., *Nature* 256:495 (1975), Coligan et al. (eds.), Current Protocols in Immunology, Vol. 1, pages 2.5.1-2.6.7 (John Wiley & Sons 1991) ["Coligan"], Picksley et al., "Production of monoclonal antibodies against proteins expressed in *E. coli*," in DNA Cloning 2: Expression Systems, 2nd Edition, Glover et al. (eds.), page 93 (Oxford University Press 1995)).

Briefly, monoclonal antibodies can be obtained by injecting mice with a composition comprising an IL-21R gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-IL-21R or anti-IL-21R heterodimer antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)).

For particular uses, it may be desirable to prepare fragments of anti-IL-21 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., Arch Biochem. Biophys. 89:230 (1960), Porter, Biochem. J. 73:119 (1959), Edelman et al., in Methods in Enzymology Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of VH and VL chains. This association can be noncovalent, as described by Inbar et al., Proc. Nat'l Acad. Sci. USA 69:2659 (1972). Alternatively, the variable chains can be linked by an intermolecular disulfide bond or cross-linked by chemicals such as glutaraldehyde (see, for example, Sandhu, Crit. Rev. Biotech. 12:437 (1992)).

The Fv fragments may comprise VH and VL chains which are connected by a peptide linker. These single-chain antigen binding proteins (scFv) are prepared by constructing a structural gene comprising DNA sequences encoding the VH and VL domains which are connected by an oligonucleotide. The structural gene is inserted into an expression vector which is subsequently introduced into a host cell, such as E. coli. The recombinant host cells synthesize a single polypeptide chain with a linker peptide bridging the two V domains. Methods for producing scFvs are described, for example, by Whitlow et al., Methods: A Companion to Methods in Enzymology 2:97 (1991) (also see, Bird et al., Science 242:423 (1988), Ladner et al., U.S. Pat. No. 4,946,778, Pack et al., Bio/Technology 11:1271 (1993), and Sandhu, supra).

As an illustration, a scFV can be obtained by exposing lymphocytes to IL-21R or an IL-21R heterodimer such as IL-21R/IL-2Rγ polypeptides in vitro, and selecting antibody display libraries in phage or similar vectors (for instance, through use of immobilized or labeled IL-22RA protein or peptide). Genes encoding polypeptides having potential IL-21R or IL-21R heterodimer binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., Phage Display of Peptides and Proteins (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using sequences comprising the IL-21R polypeptide disclosed herein to identify proteins which bind to IL-22R or an IL-21R heterodimer.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Methods in Enzymology 2:106 (1991), Courtenay-Luck, "Genetic Manipulation of Monoclonal Antibodies," in Monoclonal Antibodies: Production, Engineering and Clinical Application, Ritter et al. (eds.), page 166 (Cambridge University Press 1995), and Ward et al., "Genetic Manipulation and Expression of Antibodies," in Monoclonal Antibodies: Principles and Applications, Birch et al., (eds.), page 137 (Wiley-Liss, Inc. 1995)).

Alternatively, an anti-IL-21R or anti-IL-21R heterodimer antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989). Techniques for producing humanized monoclonal antibodies are described, for example, by Jones et al., Nature 321:522 (1986), Carter et al., Proc. Nat'l Acad. Sci. USA 89:4285 (1992), Sandhu, Crit. Rev. Biotech. 12:437 (1992), Singer et al., J. Immun. 150:2844 (1993), Sudhir (ed.), Antibody Engineering Protocols (Humana Press, Inc. 1995), Kelley, "Engineering Therapeutic Antibodies," in Protein Engineering: Principles and Practice, Cleland et al. (eds.), pages 399-434 (John Wiley & Sons, Inc. 1996), and by Queen et al., U.S. Pat. No. 5,693,762 (1997).

Moreover, anti-IL-21R or anti-IL-21R heterodimer antibodies or antibody fragments of the present invention can be PEGylated using methods in the art and described herein.

Polyclonal anti-idiotype antibodies can be prepared by immunizing animals with anti-IL-21R or anti-IL-21R heterodimer antibodies or antibody fragments, using standard techniques. See, for example, Green et al., "Production of Polyclonal Antisera," in Methods In Molecular Biology: Immunochemical Protocols, Manson (ed.), pages 1-12 (Humana Press 1992). Also, see Coligan at pages 2.4.1-2.4.7. Alternatively, monoclonal anti-idiotype antibodies can be prepared using anti-IL-22RA antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

The antibodies of the present invention include derivatives that are modified, i.e, by the covalent attachment of any type of molecule to the antibody such that covalent attachment does not prevent the antibody from binding to the IL-21 receptor or an IL-21 receptor heterodimer, such as IL-21 receptor/IL-2Rγ, or preventing receptor activation. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Anti-IL-21R or anti-IL-21R heterodimer antibodies can be conjugated with a detectable label to form an anti-IL-21R or anti-IL-21R heterodimer immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-IL-21 or anti-IL-21R heterodimer immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-IL-21R or anti-IL-21R heterodimer immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-IL-21R or anti-IL-21R heterodimer immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-21R or anti-IL-21R heterodimer immunoconjugates can be detectably labeled by linking an anti-IL-21R or anti-IL-21R heterodimer antibody component to an enzyme. When the anti-IL-21R or anti-IL-21R heterodimer enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-21R or anti-IL-21R heterodimer antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-IL-21R or anti-IL-21R heterodimer antibodies that have been conjugated with avidin, streptavidin, and biotin (see, for example, Wilchek et al. (eds.), "Avidin-Biotin Technology," Methods In Enzymology, Vol. 184 (Academic Press 1990), and Bayer et al., "Immunochemical Applications of Avidin-Biotin Technology," in Methods In Molecular Biology, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in Monoclonal Antibodies: Production, Engineering, and Clinical Application, Ritter and Ladyman (eds.), pages 180-208, (Cambridge University Press, 1995), Perry, "The Role of Monoclonal Antibodies in the Advancement of Immunoassay Technology," in Monoclonal Antibodies: Principles and Applications, Birch and Lennox (eds.), pages 107-120 (Wiley-Liss, Inc. 1995), and Diamandis, Immunoassay (Academic Press, Inc. 1996).

Pharmaceutical Compositions

The present invention further includes pharmaceutical compositions, comprising a pharmaceutically acceptable carrier and a polypeptide or antibody described herein. The pharmaceutical composition can include additional therapeutic agents, including but not limited to cytotoxic agents a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). For example, the pharmaceutical composition can comprise a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

For purposes of therapy, anti-IL-21 receptor antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising anti-IL-21 receptor antibody can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in Drug Delivery Systems, Ranade and Hollinger (eds.), pages 95-123 (CRC Press 1995); Bremer et al., "Protein Delivery with Infusion Pumps," in Protein Delivery: Physical Systems, Sanders and Hendren (eds.), pages 239-254 (Plenum Press 1997); Yewey et al., "Delivery of Proteins from a Controlled Release Injectable Implant," in Protein Delivery: Physical Systems, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in Drug Delivery Systems, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., Liposomes In Cell Biology And Pharmacology (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287, 1997; Murahashi et al., *Biol. Pharm. Bull.* 20:259, 1997). Similarly, Wu et al., *Hepatology* 27:772, 1998, have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259, 1997). Polyaconitylated human serum albumin liposomes provide another approach for targeting liposomes to liver cells (Kamps et al., *Proc. Nat'l Acad. Sci. USA* 94:11681, 1997). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99, 1998). After plasma elimination of free antibody, streptavidin-conjugated liposomes are administered. In another approach, targeting antibodies are directly attached to liposomes (Harasym et al., ibid. (1998)).

Polypeptides and antibodies can be encapsulated within liposomes using standard techniques of protein microencapsulation (see, for example, Anderson et al., *Infect. Immun.* 31:1099, 1981, Anderson et al., *Cancer Res.* 50:1853, 1990, and Cohen et al., *Biochim. Biophys. Acta* 1063:95, 1991, Alving et al. "Preparation and Use of Liposomes in Immunological Studies," in Liposome Technology, 2nd Edition, Vol. III, Gregoriadis (ed.), page 317 (CRC Press 1993), Wassef et al., Meth. *Enzymol.* 149:124, 1987). As noted above, therapeutically useful liposomes may contain a variety of components. For example, liposomes may comprise lipid derivatives of poly(ethylene glycol) (Allen et al., *Biochim. Biophys. Acta* 1150:9, 1993).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332, 1995; Ranade, "Role of Polymers in Drug Delivery," in Drug Delivery Systems, Ranade and Hollinger (eds.), pages 51-93 (CRC Press 1995); Roskos and Maskiewicz, "Degradable Controlled Release Systems Useful for Protein Delivery," in Protein Delivery: Physical Systems, Sanders and Hendren (eds.), pages 45-92 (Plenum Press 1997); Bartus et al., *Science* 281:1161, 1998; Putney and Burke, *Nature Biotechnology* 16:153, 1998; Putney, *Curr. Opin. Chem. Biol.* 2:548, 1998). Polyethylene glycol (PEG)-coated nanospheres can also provide carriers for intravenous administration of therapeutic proteins (see, for example, Gref et al., *Pharm. Biotechnol.* 10:167, 1997).

Other dosage forms can be devised by those skilled in the art, as shown, for example, by Ansel and Popovich, Pharmaceutical Dosage Forms and Drug Delivery Systems, 5th Edition (Lea & Febiger 1990), Gennaro (ed.), Remington's Pharmaceutical Sciences, 19th Edition (Mack Publishing Company 1995), and by Ranade and Hollinger, Drug Delivery Systems (CRC Press 1996).

Pharmaceutical compositions may be supplied as a kit comprising a container that comprises a neutralizing anti-IL-21 receptor, or anti-IL-21 receptor complex, antibody. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition.

A pharmaceutical composition comprising anti-IL-21 receptor antibodies can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239,1997; Ranade, "Implants in Drug Delivery," in Drug Delivery Systems, Ranade and Hollinger (eds.), pages 95-123 (CRC Press 1995); Bremer et al., "Protein Delivery with Infusion Pumps," in Protein Delivery: Physical Systems, Sanders and Hendren (eds.), pages 239-254 (Plenum Press 1997); Yewey et al., "Delivery of Proteins from a Controlled Release Injectable Implant," in Protein Delivery: Physical Systems, Sanders and Hendren (eds.), pages 93-117 (Plenum Press 1997)). Other solid forms include creams, pastes, other topological applications, and the like.

Therapeutic Uses for Anti-IL-21 Receptor Antibodies

Anti-IL-21 receptor or anti-IL-21 receptor heterodimeric polypeptides, such as anti-IL-21 receptor/IL-2Rγ binding polypeptides, would be useful for inhibiting IL-21 activity as well as receptor activity or protein-binding. Antibodies raised to the heterodimer or multimeric combinations of the present invention are preferred embodiments, as they may act more specifically against the IL-21, or more potently than antibodies raised to only one subunit. Moreover, the antagonistic and binding activity of the antibodies of the present invention can be assayed in the IL-21 proliferation and other biological assays described herein.

Antibodies to IL-21 receptor, or IL-21 receptor heterodimeric polypeptide, such as IL-21 receptor/IL-2Rγ may be used for tagging cells that express IL-21 receptor or IL-21 receptor heterodimeric polypeptides, such as IL-21 receptor/IL-2Rγ; for isolating cells that express IL-21 receptor or IL-21 receptor heterodimeric polypeptide, such as IL-21 receptor/IL-2Rγ polypeptide by affinity purification; for diagnostic assays for determining circulating levels of cells that express IL-21 receptor or IL-21 receptor heterodimeric polypeptide, such as IL-21 receptor/IL-2Rγ polypeptides; for detecting or quantitating cells that express IL-21 receptor or IL-21 receptor heterodimeric polypeptide, such as IL-21 receptor/IL-2Rγ as marker of underlying pathology or disease; in analytical methods employing FACS; for screening expression libraries; for generating anti-idiotypic antibodies; and as neutralizing antibodies or as antagonists to block IL-21 receptor or IL-21 receptor heterodimeric polypeptide, such as IL-21 receptor/IL-2Rγ, or IL-21 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-21 receptor or IL-21 receptor heterodimeric polypeptide, such as IL-21 receptor/IL-2Rγ or fragments thereof may be used in vitro to detect denatured or non-denatured IL-21 receptor or IL-21 receptor heterodimeric polypeptide, such as IL-21 receptor/IL-2Rγ or fragments thereof in assays, for example, Western Blots or other assays known in the art.

Antibodies to IL-21 receptor or IL-21 receptor heterodimeric polypeptide, such as IL-21 receptor/IL-2Rγ, are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of the IL-21.

Suitable detectable molecules may be directly or indirectly attached to polypeptides that bind IL-21 receptor or IL-21 receptor heterodimeric polypeptide, such as IL-21 receptor/IL-2Rγ antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, antibodies to IL-21 receptor or IL-21 receptor heterodimeric polypeptide, such as IL-21 receptor/IL-2Rγ, can be used for enhancing in vivo killing of target tissues (for example, blood, lymphoid, colon, and bone marrow cancers), if the binding polypeptide-cytokine or anti-IL-21 receptor or anti-IL-21 receptor heterodimeric polypeptide, such as anti-IL-21 receptor/IL-2Rγ antibody targets the hyperproliferative cell (See, generally, Hornick et al., *Blood* 89:4437-47, 1997). The described fusion proteins enable targeting of a cytokine to a desired site of action, thereby providing an elevated local concentration of cytokine. Suitable anti-IL-21 receptor homodimer and heterodimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, IL-21 antagonists, including antibodies to IL-21 receptor or IL-21 receptor heterodimeric polypeptide, such as IL-21 receptor/IL-2Rγ receptors, in conjunction with other cytokines may enable selective activation, enhancement, or selective suppression, of the immune system in conjunction with IL-21 on other cytokines which would be important in boosting immunity to infectious diseases, treating immunocompromised patients, such as HIV+ patient, or in improving vaccines. In particular, IL-21 receptor antagonists, including anti-IL-21 receptor or anti-IL-21 receptor heterodimeric polypeptide, such as anti-IL-21 receptor/IL-2Rγ, could prevent the expansion of a subset of the immune system involving IL-21 (e.g., NK cells and mature B-cells), while enabling expansion of progenitors induced by other cytokines (e.g., T-cells), and would provide therapeutic value in treatment of viral infection and other infection. For example, with Dengue virus infection, which causes dengue hemorrhagic fever/Dengue Shock syndrome (DHF/DSS) it is believed that severe DHF/DSS occurs as a result of "immune enhancement" i.e., enhanced replication of the virus in the presence of pre-existing antibodies against another serotype. In the second infection by a different Dengue virus serotype, the immune system raises antibodies against the first virus that cross-react but do not neutralize the virus, and that potentially aid its entry into macrophages. Thus, suppression of the antibody immune response, or B cell response, during a second or third Dengue infection may help the immune system react appropriately in the second infection to neutralize the virus by suppressing the "enhancing" antibodies from the first serotpye infection, and consequently avoiding severe DHF/DSS. For review, see White, D. O. and Fenner F. J. (Eds.) *Medical Virology*, $_3$rd ed., Academic Press, Orlando Fla., 1986, pages 479-508). Similarly, suppression of maternal antibody responses against fetal antigens by receptors of the present invention can aid in preventing birth defects and spontaneous abortion. Moreover, in such applications the receptors of the present invention can be used in conjunction with other cytokines to suppress some immune system activities (e.g., B-cell proliferation, using the receptors) but allowing others to increase, e.g., in the presence of other cytokines described herein and known in the art.

A therapeutically effective amount of an anti-IL-21R, or an anti-IL-21R complex, antibody refers to an amount of antibody which when administered to a subject is effective to prevent, delay, reduce or inhibit a symptom or biological activity associated with a disease or disorder. Administration may consist of a single dose or multiple doses and may be given in combination with other pharmaceutical compositions.

The present invention provides compositions and methods for using IL-21R, or IL-21R complex, antagonists in inflammatory and immune diseases or conditions such as pancreatitis, type I diabetes (IDDM), Graves Disease, inflammatory bowel disease (IBD), Crohn's Disease, multiple sclerosis, rheumatoid arthritis, diverticulosis, systemic lupus erythematosus, psoriasis, ankylosing spondylitis, scleroderma, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versous host disease, host versus graft disease, atopic dermatitis, ulcerative colitis, and asthma.

Contact Dermatitis

Allergic contact dermatitis is defined as a T cell mediated immune reaction to an antigen that comes into contact with the skin. The CLA+ T cell population is believed to be involved in the initiation of dermatitis since allergen dependent T cell responses are largely confined to the CLA+ population of cells (See Santamaria-Babi, L. F., et al., *J Exp Med* 181:1935, (1995)). Recent data have found that only memory (CD45RO+) CD4+ CLA+ and not CD8+ T cells proliferate and produce both type-1 (IFN-?) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol* 51:32, (2004).

In animal models, it has been demonstrated that allergic contact dermatitis is T cell-dependent and that the allergic-responsive T cells migrate to the site of allergen application. See generally: Engeman T. M., et al., *J Immunol* 164:5207, (2000); Ferguson T. A. & Kupper T. S. *J Immunol* 150:1172, (1993); and Gorbachev A. V. & Fairchild R. L. *Crit Rev Immunol.* 21:451(2001).

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J. M., *Arch Dermatol* 135:1551 (1999). Histopathology reveals spongiosis, hyperparakeratosis and focal parakeratosis in acute lesions, whereas marked epidermal hyperplasia with hyperparakeratosis and parakeratosis, acanthosis/hypergranulosis and perivascular infiltration of the dermis with lymphocytes and abundant mast cells are the hallmarks of chromic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol* 14:13, (2004)). A significant increase in circulating CLA+ T cells among AD patients compared with control individuals has been documented (See Teraki Y., et al., *Br J Dermatol* 143:373 (2000), while others have demonstrated that memory CLA+ T cells from AD patients preferentially respond to allergen extract compared to the CLA− population (See Santamaria-Babi, L. F., et al., *J Exp Med.*181:1935, (1995)). In humans, the pathogenesis of atopic disorders of the skin have been associated with increases in CLA+ T cells that express increased levels of Th-2-type cytokines like IL-5 and IL-13. See Akdis M., et al., *Eur J Immunol* 30:3533 (2000); and Hamid Q., et al., *J Allergy Clin Immunol* 98: 225 (1996).

NC/Nga mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy* 58:139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101:1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002).

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of anti-IL-21R, or anti-IL-21R complex, antibodies to these CIA model mice are used to evaluate the use of anti-IL-21R, or anti-IL-21R complex, antibodies to ameliorate symptoms and alter the course of disease.

Inflammatory Bowel Disease. IBD

In the United States approximately 500,000 people suffer from inflammatory bowel disease (IBD) which can affect either colon and rectum (ulcerative colitis) or both, small and large intestine (Crohn's Disease). The pathogenesis of these diseases is unclear, but they involve chronic inflammation of the affected tissues. Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intem. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-IL-21R, or anti-IL-21R complex, antibodies to these TNBS, DSS or CD4 transfer models can be used to evaluate the use of IL-21 antagonists to ameliorate symptoms and alter the course of gastrointestinal disease. IL-21 may play a role in the inflammatory response in colitis, and the neutralization of IL-21 activity by administrating IL-21 antagonists (such as anti-IL-21R, or anti-IL-21R complex, antibodies) is a potential therapeutic approach for IBD.

Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. Anti-IL-21R, or anti-IL-21R complex, antibodies of the present invention, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy. Anti-IL-21R, or anti-IL-21R complex, antibodies can be tested using a recently developed a model of psoriasis based on the CD4+CD45RB transfer model (Davenport et al., *Internat. Immunopharmacol.*, 2:653-672, 2002).

In addition to other disease models described herein, the activity of anti-IL-21 antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in ther art may be used to evaluate IL-21 antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated hereing by reference). Similarly, tissues or cells derived from human colitis, IBD, arthritis, or other inflammatory lestions can be used in the SCID model to assess the anti-inflammatory properties of the anti-IL-21 antibodies described herein.

Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol. Immunol.* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model.

Systemic Lupus Erythematosus

Systemic lupus erythematosus (SLE) is an immune-complex related disorder characterized by chronic IgG antibody production directed at ubiquitous self antigens (anti-dsDNA). The effects of SLE are systemic, rather than localized to a specific organ. Multiple chromosomal loci have been associated with the disease and may contribute towards different aspects of the disease, such as anti-dsDNA antibodies and glomerulonephritis. CD4+ T cells have been shown to play an active part in mouse models of SLE (Horwitz, *Lupus* 10:319-320, 2001; Yellin and Thienel, *Curr. Rheumatol. Rep.*, 2:24-37, 2000). The role for CD8+ T cells is not clearly defined, but there is evidence to suggest that "suppressor" CD8+ T cell function is impaired in lupus patients (Filaci et al., *J. Immunol.*, 166:6452-6457, 2001; Sakane et al, *J. Immunol.*, 137: 3809-3813, 1986).

IL-21 has been shown to modulate antibody responses by directly acting on B cells. (Mehta et al., *J. Immunol.*, 170: 4111-4118, 2003; Ozaki et al., *Science*, 298:1630-1634, 2002; Suto et al., *Blood*, 100:4565-4573, 2002). For example, Ozaki et al., (*J. Immunol.* 173:5361, 2004) demonstrated that in BXSB-Yaa mice, a model for SLE, there is an elevated IL-21 level. Moreover, because IL-21 enhances CD8 T cell activity, administration of anti-IL-21 antibodies would provide a more robust T cell suppressor function in lupus patients where that function is compromised.

Anti-IL-21R, or anti-IL-21R complex, antibodies can be administered in combination with other agents already in use in autoimmunity including immune modulators such as IFN-α, IFNγ, NOVANTRONE®, ENBREL®, REMICADE®, LEUKINE® and IL-2. Establishing the optimal dose level and scheduling for anti-IL-21R, or anti-IL-21R complex, antibodies is done by a variety of means, including study of the pharmacokinetics and pharmacodynamics of anti-IL-21R, or anti-IL-21R complex, antibodies; determination of effective doses in animal models, and evaluation of the toxicity of anti-IL-21R, or anti-IL-21R complex, antibodies. Direct pharmacokinetic measurements done in primates and clinical trials can then be used to predict theoretical doses in patients that achieve plasma anti-IL-21R, or anti-IL-21R complex, antibody levels that are of sufficient magnitude and duration to achieve a biological response in patients.

The invention is further illustrated by the following non-limiting examples.

EXAMPLES

Example 1

Production of IL-21

IL-21 protein was produced as described in U.S. Patent Application No. 2006-0134754 and WO 04/055168, incorporated in its entirety herein. Briefly, an IL-21 nucleotide sequence was optimized and inserted in an *E. coli* expression vector which was deposited as ATCC Accession No. PTA-4853. The expression vector was introduced into *E. coli* strain W3110 (ATCC Accession No. 27325).

Host cells were fermented by growing *E. coli* strains expressing IL-21 in a suitable medium in shake flask culture to in a suitable medium and may be supplemented with carbohydrates, such as fructose, glucose, galactose, lactose, and glycerol. Isopropyl thiogalactopyranoside (IPTG) is may be added to the culture to a concentration 0. 1 to 2.0 mM.

Following fermentation the cells were harvested by centrifugation, re-suspended in homogenization buffer and homogenized. After the homogenate was collected, it was resuspended a guanidine containing solution and the supernatant containing solubilized IL-21 was decanted and retained. The concentration of the IL-21 in the solubilized fraction was determined by reversed phase HPLC. Once the inclusion bodies were solubilized and denatured in guanidine solution containing a reducing agent, the reduced IL-21 was then oxidized in a controlled renaturation step. This step involved dilution in a refold buffer containing arginine hydrochloride, salts, and an oxido-shuffling system.

Purification of IL-21 protein may include purification of the IL-21 using hydrophobic interaction chromatography. The IL-21 may be further purified by high performance cation exchange chromatography. The methods for purifying IL-21 can comprise concentrating and carrying out a buffer exchange of the protein. This step is designed to concentrate the high performance cation exchange column eluate and exchange it into formulation buffer. The final column eluate pool is concentrated to increase the concentration of IL-21. Further purification of IL-21 to remove the remaining impurities and contaminants may be desirable. For example, an anion exchange column can be used to reduce the endotoxin level.

Example 2

Production of Recombinant IL-21 and IL-21 Receptor Proteins

A. The IL-21 receptor (also designated as zalpha11 or IL-21r) heterodimer protein can be produced as described in U.S. Patent Application No. 2002-0137677, incorporated in its entirety herein. Briefly, a vector expressing a secreted human hzalpha11hIL2Rgamma heterodimer is constructed. In this construct, the extracellular domain of hzalpha 11 is fused to the CH1 domain of IgG γ1. The CH1 domain is cloned into a mammalian expression vector. The CL1 domain of the human κ light chain is cloned in a mammalian expression vector.

A construct having human zalpha11 fused to CH1 is made, and the vector is sequenced to confirm that the fusion is correct. A separate construct having hIL2Rgamma fused to CL1 can be also constructed. The resulting vector is sequenced to confirm that the human IL-2Rgamma/CL1 fusion is correct.

The human zalpha11 (IL-21r) and human IL-2Rgamma receptor fusions are co-expressed. Each expression vector is co-transfected into mammalian host cells by methods known to those skilled in the art. The transfected cells are selected for 10 days in methotrexate (MTX) and G418 (Gibco/BRL) for 10 days. The resulting pool of transfectants is selected again in MTX and G418 for 10 days.

The resulting pool of doubly-selected cells is used to generate protein. Factories (Nunc, Denmark) of this pool are used to generate conditioned medium. This serum free, conditioned media is passed over a protein-A column and eluted in fractions. Fractions found to have the highest concentration are pooled and dialyzed (10 kD MW cutoff) against PBS. Finally the dialyzed material is submitted for amino acid analysis (AAA). The purified soluble human zalpha11 receptor/IL-2Rgamma receptor can be used to assess its ability to compete for binding of the human zalpha11 Ligand a BaF3 proliferation assay.

B. The extracellular domain of human zalpha11 fused to Fc9 (Fc region of human gamma1 (Kabat numbering 221-447; Kabat et al, Sequences of Proteins of Immunological Interest, U.S. Dept. Health and Human Serv., Bethesda, Md., 1991)) with an GluGlu tag (Grussenmeyer et al., Proc. Natl. Acad. Sci. USA 82:7952-4, 198)) at the carboxyl terminus was generated by overlap PCR. The cDNA was inserted into pZMP31 (described in US Patent application, US2003/023414; a hybrid vector having a cytomegalovirus enhancer and myeloproliferative sarcoma virus promoter) by recombination in yeast. The extracellular domain of the human IL2 receptor common gamma chain was fused to Fc9 with a 6×His tag at the carboxyl terminus of Fc9. This construct was inserted into pZMP21z by yeast recombination using the same method as described for zalpha11 Fc9CEE. The resulting constructs were sequenced to verify that the inserts were correct. Both plasmids were transfected into suspension, serum-free-adapted CHO cells by electroporation and selected in protein-free PFCHO media (BioWhittaker) without hypoxanthine and thymidine with 200 ng/mL zeomycin added. These cells were then selected in the same medium plus increasing concentrations of methotrexate until the cells were resistant to both 1 uM methotrexate and 200 ng/mL zeomycin. The cells were tested for production of heterodimeric IL21 receptor by western blot analysis for the presence of both EE and his tags.

The design of zcytor26f2 (extracellular domain of the human IL2 receptor common gamma chain was fused to Fc9 with a 6×His tag) is such that three tags are available for purification (GluGlu, His, and Fc), of which two are utilized to best discriminate heterodimer from the two homodimer contaminants. All molecules containing an Fc domain (homodimer contaminants and heterodimer target) were captured and purified from host cell components and related media products. The pool containing all species was concentrated and injected over an appropriate size exclusion column (Superdex 200) in order to remove aggregates. The SEC pool containing all three species (two homodimers and one heterodimer) was subjected to Immobilized Metal Affinity Chromatography (IMAC) using the Ni counter ion under highly discriminating load and elution conditions. The IMAC elution pool contained highly pure heterodimer, with only residual homodimer contamination. IMAC pool buffer was exchanged into formulation buffer using size exclusion chromatography (Superdex 200), which also removes any residual aggregation products. This IL-21 heterodimeric protein was used as a comparator when testing an antibody's neutralizing activity.

Example 3

Preparation of IL-21 Monoclonal Antibodies

Rat monoclonal antibodies are prepared by immunizing 4 female Sprague-Dawley Rats (Charles River Laboratories, Wilmington, Mass.), with the purified recombinant IL-21 receptor protein. One with ordinary skill in the art will readily recognize that, because the extracellular domain is the epitopic domain, the methods described herein can be used to produce the antibody to soluble as well as insoluble IL-21R proteins. Therefore, this Example, and all following Examples, provide support for not only antibodies to a receptor complex comprising soluble IL-21 receptor but also insoluble IL-21 receptor (SEQ ID NO:2). The rats are each given an initial intraperitoneal (IP) injection of 25 μg of the purified recombinant protein in Complete Freund's Adjuvant (Pierce, Rockford, Ill.) followed by booster IP injections of 10 μg of the purified recombinant protein in Incomplete Freund's Adjuvant every two weeks. Seven days after the administration of the second booster injection, the animals are bled and serum is collected.

The IL-21-specific rat sera samples are characterized by ELISA using 1 ug/ml of the purified recombinant IL-21 receptor protein as the specific antibody target.

Splenocytes are harvested from a single high-titer rat and fused to SP2/0 (mouse) myeloma cells using PEG 1500 in a single fusion procedure (4:1 fusion ratio, splenocytes to myeloma cells, "Antibodies: A Laboratory Manual, E. Harlow and D. Lane, Cold Spring Harbor Press). Following 9 days growth post-fusion, specific antibody-producing hybridoma pools are identified by radioimmunoprecipitation (RIP) using the $^{125}$Iodine-labeled recombinant IL-21R protein as the specific antibody target and by ELISA using 500 ng/ml of the recombinant IL-21R protein as specific antibody target. Hybridoma pools positive in either assay protocol are analyzed further for their ability to block the cell-proliferative activity ("neutralization assay") of purified recombinant IL-21 protein on Baf3 cells expressing the IL-21 receptor sequence.

Hybridoma pools yielding positive results by RIP only or RIP and the "neutralization assay" are cloned at least two times by limiting dilution.

The monoclonal antibodies produced by clones are characterized in a number of ways including binning (i.e, determining if each antibody could inhibit the binding of any proteins other than the intended inhibited protein binding, IL-21 to IL-21R or IL-21R/IL-2Rγ), relative affinity, and neutralization. Monoclonal antibodies purified from tissue culture media are characterized for their ability to block the cell-proliferative activity ("neutralization assay") of purified recombinant IL-21R on Baf3 cells expressing the receptor sequences. "Neutralizing" monoclonal antibodies are identified in this manner.

Samples were taken and assayed using both the neutralization assay and a direct titration ELISA. In this assay a sample was titrated out using four-fold serial dilutions to see which clone could maintain the highest OD reading. Using the results from both the neutralization and titration assays, specific clones from each initial master well were chosen to go forward with. Another neutralization screen was performed that ran all these samples in the same assay and at this point the number of cell lines was narrowed down to four top picks. These were subjected to an additional round of cloning to ensure culture homogeneity and screened using the direct ELISA. After one more titration assay, two final IL-21 clones were chosen and designated 268.5.1.11.42.1.4.3.9 (ATCC Accession No. PTA-7143) and 272.21.1.3.4.2 (ATCC Accession No. PTA-7142). An anti-IL-21 receptor monoclonal antibody was also selected and deposited under the designation 285.134.3.22 (ATCC Accession NO. PTA-7141). The monoclonal antibodies produced by these hybridoma clones can be cultured in a growth medium of 90% Iscove's Modified Dulbecco's medium with 2 mM L-glutamine, 100 μg/mL penicillin, and 100 μg/mL streptomycin sulfate, and 10% Fetal Clone I Serum (Hyclone Laboratories). The clones can be propogated by starting cultures at 2×105 cells/mland maintaining between 1×105 and 5×105 cell/ml at 37° C. and 5-6% CO. Cells ca be adapted to serum free conditions upon subsequent transfers. Cells that are frozen are stored in 90% serum, 10% DMSO and stored in vapor phase of liquid nitrogen freezer.

In addition, BALB/c mice and IL-21 knockout mice are immunized with IL-21 or IL-21 receptor protein to produce monoclonal antibodies.

Example 4

Serum Screening of Monoclonal Antibodies

The activity of anti-IL-21 antibodies is measured using a cell-based potency bioassay. The bioassay utilizes a BaF3 reporter cell line that was engineered to express the IL-21 receptor (IL-21R) through stable transfection with IL-21R cDNA. The IL-21R/BaF3 transfected cells are highly dependent upon IL-3 for growth and, in their absence, are unable to proliferate and undergo apoptosis within 24 hours. In the cell-based bioassay, the IL-21R/BaF3 transfected cells are incubated with varying concentrations of serum containing anti-IL-21 antibodies in the presence of 10-20 ng/ml of IL-21, and subsequent cellular proliferation is measured.

Example 5

Characterization of Antibodies

Epitope Binning

Epitope binning studies are performed on a Biacore1000™ system (Biacore, Uppsalla Sweden). Methods are programmed using Method Definition Language (MDL) and run using Biacore Control Software, v 1.2. Polyclonal goat anti-Mouse IgG Fc antibody (Jackson ImmunoResearch Laboratories, West Grove, Pa.) is covalently immobilized to a Biacore CM5 sensor chip and is used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, IL-21R is injected and allowed to specifically bind to the captured primary monoclonal antibody. The Biacore instrument measures the mass of protein bound to the sensor chip surface, and thus, binding of both the primary antibody and IL-21R antigen are verified for each cycle. Following the binding of the primary antibody and antigen to the chip, a monoclonal antibody of the test series is injected as the secondary antibody, and allowed to bind to the pre-bound antigen. If the secondary monoclonal antibody is capable of binding the IL-21R antigen simultaneously with the primary monoclonal antibody, an increase in mass on the surface of the chip, or binding, is detected. If, however, the secondary monoclonal antibody is not capable of binding the IL-21R antigen simultaneously with the primary monoclonal antibody, no additional mass, or binding, is detected. Each monoclonal antibody tested against itself is used as the negative control to establish the level of the background (no-binding) signal. Data are compiled using BioEvaluation 3.2 RCI software, then loaded into Excel™ for data processing.

Western Blotting

The ability of the neutralizing monoclonal antibodies from clones to detect denatured and reduced/denatured IL-21R polypeptides from two sources is assessed using a Western blot format. A rabbit polyclonal antibody known to detect IL-21R, or an IL-21R complex such as IL-21 R/IL/2rγ, in a Western blot format is used as a positive control.

The IL-21R protein is loaded onto 4-12% NuPAGE Bis-Tris gels (Invitrogen, Carlsbad, Calif.) in either non-reducing or reducing sample buffer (Invitrogen) along with molecular weight standards (SeeBlue; Invitrogen), and electrophoresis is performed. Following electrophoresis, protein is transferred from the gel, the nitrocellulose blots are blocked overnight and exposed to each antibody. The blots are then probed with a secondary antibody conjugated to horseradish peroxidase; sheep anti-mouse IgG-HRP (Amersham: Piscataway, N.J.) for the monoclonal antibodies and donkey anti-rabbit Ig-HRP (Amersham) for the polyclonal antibodies. Bound antibody is detected using a chemiluminescent reagent (Lumi-Light Plus Reagent: Roche, Mannheim, Germany) and images of the blots were recorded on a Lumi-Imager (Mannheim-Boehringer).

Example 6

DTH Mouse Model

DTH responses are classic immune responses that are initiated by CD4+ T cells and mediated by T cells, neutrophils and macrophages. A DTH response is a good indicator of a CD4+ T cell mediated response. Mice are immunized subcutaneously with chicken ovalbumin protein (OVA) in either of 2 adjuvants, RIBI or CFA. This phase is called the sensitization phase (days 0-6). Ear measurements are taken seven days later. Mice are then injected in the ear with control PBS (left ear) or OVA (right ear). This phase is called the challenge phase (days 7-8). Immune responses generated to OVA induce inflammation in the ear resulting an increase in ear thickness in 24 hours in the OVA-treated, but not in the PBS-treated ear. This is measured using calipers.

C57BL/6 mice (n=8/group) are immunized in the back with 100 μg chicken ovalbumin (OVA) emulsified in RIBI adjuvant (Corixa, Seattle, WA) in a total volume of 200 μl. A 0.5 mg/ml of ovalbumin is added to a single vial of RIBI and vortexed vigorously for 2 minutes to form an emulsion that is used to inject mice. Seven days after the immunization, mice are injected with 10 μl PBS in the left ear (control) and with 10 μg OVA in PBS in the right ear in a volume of 10 μl. Ear thickness of all mice is measured before injecting mice in the ear (0 measurement). Ear thickness is measured 24 hours after challenge. The difference in ear thickness between the 0 measurement and the 24 hour measurement is calculated and is reflective of the inflammation in the ear. Groups of mice are injected with PBS or different concentration of anti-IL-21 antibody intra-peritoneally from either days 0-6 (sensitization phase) or from days 7-8 (challenge phase). The injection on day 7 and 8 is given 2 hours before measuring ear thickness at the 0 and 24 hour time points. At the end of the 24 hour period, once ear thickness is measured, the ears were cut and placed in formalin for histological analysis.

Example 7

Mouse Model for Multiple Sclerosis

To test whether an antibody to IL-21R or an IL-21R complex affects multiple sclerosis, the ability of anti-IL-21R antibodies to inhibit experimental autoimmune encephalomyelitis (EAE), a mouse model for MS, is tested. The well characterized myelin oligodendrocyte glycoprotein (MOG) 35-55 peptide immunization model in C57BL/6 mice is used. The experiment is run to determine that anti-IL-21 antibody could delay and/or inhibit disease scores in EAE either by inhibiting DC mediated antigen presentation or by enhancing CD8 T cell responses. Absence of efficient CD8 T cell responses in this model exacerbates EAE (Malipiero et. al., *Eur. J. Immunol.*, 27:3151-3160, 1997). Delayed onset of disease in the EAE model in a dose dependent manner suggests that use of anti-IL-21 antibody may be beneficial in MS.

Experimental autoimmune encephalomyelitis (EAE) is a mouse model for MS. In one such model, C57BL/6 mice are immunized with 100 μg MOG pepetide (MOG35-55) or 100 μg recombinant MOG protein emulsified in RIBI adjuvant. Two milliliters of a 0.5 mg/ml preparation of the MOG35-55 in PBS is added to a vial of RIBI and vortexed vigorously to emulsify the solution or a 1:1 ratio of recombinant MOG in DFA is prepared. The backs of mice are shaved and 100 μg MOG/RIBI is injected s.c in the backs of mice. The mice are weighed two days before and every day after the immunization. Mice are then injected on day 2 i.v with 200 μl pertussis toxin (PT), a final concentration of 200 ng/mouse. Mice are monitored daily for clinical scores. Groups of mice are injected i.p. with 200 μl PBS, 100 μg BSA, 10 μg-200 μg anti-IL-21 antibody in a 200 μl volume from days 0-20, or 3× a week for 3 weeks. The weights of mice, clinical scores and incidence are evaluated and plotted for analysis.

Example 8

CD4+CD45RBhi (CD25−) Colitis and Psoriasis Mouse Model

Transfer of CD4+ CD45RBhi or CD4+CD25− T cells into syngenic SCID mice results in colitis in the mice. Co-transfer of regulatory T cells (CD4+CD25+ or CD4+CD45RBlo) inhibits this colitis. After transfer of CD4+CD25− T cells into mice, if mice are additionally injected with staphylococcal enterotoxin B (SEB), mice not only develop colitis, but also psoriasis. Anti-IL-21 antibody is administered from days 0-21 after cell transfer and symptoms for colitis and psoriasis are monitored. Inhibition of psoriatic score or colitis (histology) indicates that anti-IL-21 antibody can inhibit these autoimmune diseases.

Spleens and inguinal lymph nodes are isolated from B10.D2 mice. Single cell suspensions are formed and counted. Using the Miltenyi Bead system, CD25+ cells are sorted out by positive selection. Cells are stained with CD25-PE (BD Pharmingen) at 1:100 dilution and incubated for 15 minutes. Excess antibody is washed out and the cells are incubated with 10 ul anti-PE beads/106 cells for 20 minutes. The cells are washed with PBS and passed over an LS column (Miltenyi Biotech). Cells that pass through the column (CD25−) are retained for further analysis. A CD4 enrichment cocktail (Stem Cell technologies) is added (1:100) to these CD25− cells and incubated for 15 minutes. Cells are washed with PBS. A 1:10 dilution of anti-biotin tetramer is added to the cells for 15 minutes followed by a magnetic colloid (60ul/106 cells) for 15 minutes (all from Stem Cell Technologies). Cells are passed through a negative selection column (0.5", Stem cell Technologies). Cells that pass through are the CD4+ CD25− cells. Purity is analyzed using flow cytometry. 0.4× 106 cells are injected i.v into naïve CB-17 SCID mice in a total volume of 200 µl. Mice are injected i.p with 10 µg SEB the following day (d1). Symptoms for psoriasis and colitis are followed from 2-5 weeks. Groups of mice are injected i.p. with PBS, 100 µg BSA or 10-200 µg IL-21R or IL-21R complex from days 1-20, or 3× a week for 3 weeks.

Inhibition of psoriatic and colitis symptoms in anti-IL-21R, or anti-IL-21R complex, antibody treated mice indicates that anti-IL-21R, or anti-IL-21R complex, antibodies can inhibit autoimmune symptoms in this model for psoriasis and colitis.

Example 9

Contact Hypersensitivity Mouse Model

Contact hypersensitivity can be induced in mice using a variety of contact allergens including dinitrofluorobenzene (DNFB) and oxazolone. Mice are sensitized topically with the allergen in a vehicle of acetone and olive oil and then challenged in the ear with the allergen in olive oil alone. Change in ear thickness is a measure of the immune response against the allergen. Anti-IL-21R or anti-IL-21R complex antibodies are administered either at the sensitization phase (d0-5) or during the challenge phase (d5-6). Inhibition of ear thickness by IL-21R, or IL-21R complex, indicates a role for IL-21R polypeptides in inhibiting contact hypersensitivity.

C57B1/6 mice are painted in the back with 0.5% DNFB in acetone:olive oil (4:1) or acetone:olive oil alone on d0. On d5, ear thickness of mice is measured using calipers and mice are challenged in the ears with olive oil alone (control) or 0.25% DNFB in olive oil by dropping a 25 µl solution onto the ear. Change in ear thickness is measured on d6 and the inflammation calculated as a difference in ear thickness between d5 and d6. Groups of mice are injected i.p. with PBS or 10-100 µg anti-IL-21R, or anti-IL-21R complex, antibodies on either days 0-5 or days 5-6.

Inhibition of ear thickness by anti-IL-21R, or anti-IL-21R complex, antibodies demonstrate that anti-IL-21R, or anti-IL-21R complex, antibodies can be useful in inhibiting contact hypersensitivity.

Example 10

Phosphorylated-STAT3 Assay for Detection of IL-21 Neutralization

Previously derived Baf3/human IL21 receptor (hIL-21R) transfectants were used (see, U.S. Pat. Nos. 6,307,024 and 6,686,178, incorporated herein by reference). The cells were washed three times in Baf3 bioassay media which consists of: RPMI, 1×Glutamax, 10% Fetal Bovine Serum, 50 uM Beta-mercaptoethanol, 200 ug/mL Zeocin, 1 mg/mL G418 (all from Invitrogen Corporation, Carlsbad, Calif.). After third wash, cells were counted using standard methods (hemacytometer) and resuspended to $6 \times 10^5$ cells per mL in bioassay media. Cells were then plated in a 96-well round bottom tissue culture plate at 30,000 cells per well. The plate was then transferred to a 37° C. tissue culture incubator while the other assay plates were set up.

The samples plate was then set up with 30 uL of 2.0 ng/mL human IL-21 plus 30 uL of one of the following: diluted mouse serum (1:10, 1:50 or 1:100 final concentrations), media, anti-IL-21 neutralizing antibody (various lots and concentrations), soluble hIL-21R (example 2) or irrelevant controls. The plate was then transferred to a 37° C. incubator. After 30-40 minutes, both the cell plate and the sample plates were removed from the incubator and 50 uL of each well in the sample plate was transferred to the cell plate and mixed. The plates were then placed back in the 37° C. incubator for exactly 8 minutes. At this point, the reaction was stopped by placing the plate on ice and adding 150 uL of ice cold BioPlex Cell Wash Buffer (BioRad Laboratories, Hercules, Calif.). The plate was centrifuged for 5 minutes at 1500 RPM and 4° C. Following centrifugation, the supernatant was disgarded into the sink and cells were lysed in 60 uL BioPlex Cell Lysis Buffer containing Factor 1, Factor 2 and PMSF (all from BioRad). Lysed cells were pipetted to break up clumps and then shaken at 600 RPM on at 4° C. for 20 minutes. The plate was then centrifuged again for 20 minutes at 3000 RPM at 4° C. After centrifugation, 55 uL of lysate was removed and mixed with 55 uL of Phosphoprotein Testing Assay Buffer (BioRad).

At this point a filter plate was pre-wetted with 50 uL Phosphoprotein Wash Buffer (PWB), aspirated and 50 uL of PhosphoSTAT3 Coupled Beads (BioRad) plated. These beads were then aspirated and the plate was washed three times with 75 uL of PWB. Following final aspiration, 50 uL of diluted lysate was transferred to the plate which was then covered and shaken overnight at room temperature. The following morning, the plate was washed three times with PWB, and biotinylated-PhosphoSTAT3 Detection Antibodies (BioRad) were then added for 20 minutes at room temperature. The plate was washed three more times in PWB and then Streptavidin-PE was added for 10 minutes. Finally, the plate was washed three times with Phosphoprotein Resuspension Buffer (PRB) and the beads were resuspended in 125 uL of PRB.

Total phosphorylated-STAT3 was measured in each well by following the standard Luminex 100 data collection protocol as recommended by the manufacturer (Luminex Inc., Austin, Tex.). Data were then analyzed and expressed as fold-induction of phosphorylated-STAT3 as compared to media alone.

What is claimed is:

1. A monoclonal antibody produced by a hybridoma designated ATCC Accession NO. PTA-7141.

2. A chimeric antibody derived from the antibody of claim 1.

3. A humanized antibody derived from the antibody of claim 1.

4. The hybridoma cell producing the monoclonal antibody of claim 1.

5. A method of producing the monoclonal antibody of claim 1 comprising: culturing the hybridoma under conditions that provide for production of the monoclonal antibody by the hybridoma.

* * * * *

SEQUENCE LISTING

<160> NUMBER OF SEQ ID NOS: 10

<210> SEQ ID NO 1
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 1

```
atg ccg cgt ggc tgg gcc gcc ccc ttg ctc ctg ctg ctc cag gga      48
Met Pro Arg Gly Trp Ala Ala Pro Leu Leu Leu Leu Leu Gln Gly
 1               5                  10                  15 ggc tgg ggc tgc ccc gac ctc gtc tgc tac acc gat tac ctc cag acg      96
Gly Trp Gly Cys Pro Asp Leu Val Cys Tyr Thr Asp Tyr Leu Gln Thr
                20                  25                  30 gtc atc tgc atc ctg gaa atg tgg aac ctc cac ccc agc acg ctc acc     144
Val Ile Cys Ile Leu Glu Met Trp Asn Leu His Pro Ser Thr Leu Thr
            35                  40                  45 ctt acc tgg caa gac cag tat gaa gag ctg aag gac gag gcc acc tcc     192
Leu Thr Trp Gln Asp Gln Tyr Glu Glu Leu Lys Asp Glu Ala Thr Ser
        50                  55                  60 tgc agc ctc cac agg tcg gcc cac aat gcc acg cat gcc acc tac acc     240
Cys Ser Leu His Arg Ser Ala His Asn Ala Thr His Ala Thr Tyr Thr
65                  70                  75                  80 tgc cac atg gat gta ttc cac ttc atg gcc gac gac att ttc agt gtc     288
Cys His Met Asp Val Phe His Phe Met Ala Asp Asp Ile Phe Ser Val
                85                  90                  95 aac atc aca gac cag tct ggc aac tac tcc cag gag tgt ggc agc ttt     336
Asn Ile Thr Asp Gln Ser Gly Asn Tyr Ser Gln Glu Cys Gly Ser Phe
            100                 105                 110 ctc ctg gct gag agc atc aag ccg gct ccc cct ttc aac gtg act gtg     384
Leu Leu Ala Glu Ser Ile Lys Pro Ala Pro Pro Phe Asn Val Thr Val
        115                 120                 125 acc ttc tca gga cag tat aat atc tcc tgg cgc tca gat tac gaa gac     432
Thr Phe Ser Gly Gln Tyr Asn Ile Ser Trp Arg Ser Asp Tyr Glu Asp
130                 135                 140 cct gcc ttc tac atg ctg aag ggc aag ctt cag tat gag ctg cag tac     480
Pro Ala Phe Tyr Met Leu Lys Gly Lys Leu Gln Tyr Glu Leu Gln Tyr
145                 150                 155                 160 agg aac cgg gga gac ccc tgg gct gtg agt ccg agg aga aag ctg atc     528
Arg Asn Arg Gly Asp Pro Trp Ala Val Ser Pro Arg Arg Lys Leu Ile
                165                 170                 175 tca gtg gac tca aga agt gtc tcc ctc ctc ccc ctg gag ttc cgc aaa     576
Ser Val Asp Ser Arg Ser Val Ser Leu Leu Pro Leu Glu Phe Arg Lys
            180                 185                 190 gac tcg agc tat gag ctg cag gtg cgg gca ggg ccc atg cct ggc tcc     624
Asp Ser Ser Tyr Glu Leu Gln Val Arg Ala Gly Pro Met Pro Gly Ser
        195                 200                 205 tcc tac cag ggg acc tgg agt gaa tgg agt gac ccg gtc atc ttt cag     672
Ser Tyr Gln Gly Thr Trp Ser Glu Trp Ser Asp Pro Val Ile Phe Gln
    210                 215                 220 acc cag tca gag gag tta aag gaa ggc tgg aac cct cac ctg ctg ctt     720
Thr Gln Ser Glu Glu Leu Lys Glu Gly Trp Asn Pro His Leu Leu Leu
225                 230                 235                 240 ctc ctc ctg ctt gtc ata gtc ttc att cct gcc ttc tgg agc ctg aag     768
Leu Leu Leu Leu Val Ile Val Phe Ile Pro Ala Phe Trp Ser Leu Lys
                245                 250                 255 acc cat cca ttg tgg agg cta tgg aag aag ata tgg gcc gtc ccc agc     816
Thr His Pro Leu Trp Arg Leu Trp Lys Lys Ile Trp Ala Val Pro Ser
            260                 265                 270 cct gag cgg ttc ttc atg ccc ctg tac aag ggc tgc agc gga gac ttc     864
Pro Glu Arg Phe Phe Met Pro Leu Tyr Lys Gly Cys Ser Gly Asp Phe
        275                 280                 285 aag aaa tgg gtg ggt gca ccc ttc act ggc tcc agc ctg gag ctg gga     912
Lys Lys Trp Val Gly Ala Pro Phe Thr Gly Ser Ser Leu Glu Leu Gly
    290                 295                 300
```

```
ccc tgg agc cca gag gtg ccc tcc acc ctg gag gtg tac agc tgc cac      960
Pro Trp Ser Pro Glu Val Pro Ser Thr Leu Glu Val Tyr Ser Cys His
305                 310                 315                 320 cca cca cgg agc ccg gcc aag agg ctg cag ctc acg gag cta caa gaa     1008
Pro Pro Arg Ser Pro Ala Lys Arg Leu Gln Leu Thr Glu Leu Gln Glu
                325                 330                 335 cca gca gag ctg gtg gag tct gac ggt gtg ccc aag ccc agc ttc tgg     1056
Pro Ala Glu Leu Val Glu Ser Asp Gly Val Pro Lys Pro Ser Phe Trp
            340                 345                 350 ccg aca gcc cag aac tcg ggg ggc tca gct tac agt gag gag agg gat     1104
Pro Thr Ala Gln Asn Ser Gly Gly Ser Ala Tyr Ser Glu Glu Arg Asp
        355                 360                 365 cgg cca tac ggc ctg gtg tcc att gac aca gtg act gtg cta gat gca     1152
Arg Pro Tyr Gly Leu Val Ser Ile Asp Thr Val Thr Val Leu Asp Ala
    370                 375                 380 gag ggg cca tgc acc tgg ccc tgc agc tgt gag gat gac ggc tac cca     1200
Glu Gly Pro Cys Thr Trp Pro Cys Ser Cys Glu Asp Asp Gly Tyr Pro
385                 390                 395                 400 gcc ctg gac ctg gat gct ggc ctg gag ccc agc cca ggc cta gag gac     1248
Ala Leu Asp Leu Asp Ala Gly Leu Glu Pro Ser Pro Gly Leu Glu Asp
                405                 410                 415 cca ctc ttg gat gca ggg acc aca gtc ctg tcc tgt ggc tgt gtc tca     1296
Pro Leu Leu Asp Ala Gly Thr Thr Val Leu Ser Cys Gly Cys Val Ser
            420                 425                 430 gct ggc agc cct ggg cta gga ggg ccc ctg gga agc ctc ctg gac aga     1344
Ala Gly Ser Pro Gly Leu Gly Gly Pro Leu Gly Ser Leu Leu Asp Arg
        435                 440                 445 cta aag cca ccc ctt gca gat ggg gag gac tgg gct ggg gga ctg ccc     1392
Leu Lys Pro Pro Leu Ala Asp Gly Glu Asp Trp Ala Gly Gly Leu Pro
    450                 455                 460 tgg ggt ggc cgg tca cct gga ggg gtc tca gag agt gag gcg ggc tca     1440
Trp Gly Gly Arg Ser Pro Gly Gly Val Ser Glu Ser Glu Ala Gly Ser
465                 470                 475                 480 ccc ctg gcc ggc ctg gat atg gac acg ttt gac agt ggc ttt gtg ggc     1488
Pro Leu Ala Gly Leu Asp Met Asp Thr Phe Asp Ser Gly Phe Val Gly
                485                 490                 495 tct gac tgc agc agc cct gtg gag tgt gac ttc acc agc ccc ggg gac     1536
Ser Asp Cys Ser Ser Pro Val Glu Cys Asp Phe Thr Ser Pro Gly Asp
            500                 505                 510 gaa gga ccc ccc cgg agc tac ctc cgc cag tgg gtg gtc att cct ccg     1584
Glu Gly Pro Pro Arg Ser Tyr Leu Arg Gln Trp Val Val Ile Pro Pro
        515                 520                 525 cca ctt tcg agc cct gga ccc cag gcc agc                             1614
Pro Leu Ser Ser Pro Gly Pro Gln Ala Ser
    530                 535

<210> SEQ ID NO 2
<211> LENGTH: 538
<212> TYPE: PRT
<213> ORGANISM: Homo sapiens

<400> SEQUENCE: 2

Met Pro Arg Gly Trp Ala Ala Pro Leu Leu Leu Leu Leu Leu Gln Gly
 1               5                  10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
        50                  55                  60
```

```
Cys Ser Leu His Arg Ser Ala His Asn Ala Thr His Ala Thr Tyr Thr
 65                  70                  75                  80

Cys His Met Asp Val Phe His Phe Met Ala Asp Ile Phe Ser Val
                 85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Phe Asn Val Thr Val
            115                 120                 125

Thr Phe Ser Gly Gln Tyr Asn Ile Ser Trp Arg Ser Asp Tyr Glu Asp
            130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480
```

```
Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
            530                 535

<210> SEQ ID NO 3
<211> LENGTH: 696
<212> TYPE: DNA
<213> ORGANISM: Homo sapiens
<220> FEATURE:
<221> NAME/KEY: CDS
<222> LOCATION: (1)...(696)

<400> SEQUENCE: 3 ctg aac acg aca att ctg acg ccc aat ggg aat gaa gac acc aca gct      48
Leu Asn Thr Thr Ile Leu Thr Pro Asn Gly Asn Glu Asp Thr Thr Ala
 1               5                  10                  15 gat ttc ttc ctg acc act atg ccc act gac tcc ctc agt gtt tcc act      96
Asp Phe Phe Leu Thr Thr Met Pro Thr Asp Ser Leu Ser Val Ser Thr
                 20                  25                  30 ctg ccc ctc cca gag gtt cag tgt ttt gtg ttc aat gtc gag tac atg     144
Leu Pro Leu Pro Glu Val Gln Cys Phe Val Phe Asn Val Glu Tyr Met
             35                  40                  45 aat tgc act tgg aac agc agc tct gag ccc cag cct acc aac ctc act     192
Asn Cys Thr Trp Asn Ser Ser Ser Glu Pro Gln Pro Thr Asn Leu Thr
         50                  55                  60 ctg cat tat tgg tac aag aac tcg gat aat gat aaa gtc cag aag tgc     240
Leu His Tyr Trp Tyr Lys Asn Ser Asp Asn Asp Lys Val Gln Lys Cys
 65                  70                  75                  80 agc cac tat cta ttc tct gaa gaa atc act tct ggc tgt cag ttg caa     288
Ser His Tyr Leu Phe Ser Glu Glu Ile Thr Ser Gly Cys Gln Leu Gln
                 85                  90                  95 aaa aag gag atc cac ctc tac caa aca ttt gtt gtt cag ctc cag gac     336
Lys Lys Glu Ile His Leu Tyr Gln Thr Phe Val Val Gln Leu Gln Asp
            100                 105                 110 cca cgg gaa ccc agg aga cag gcc aca cag atg cta aaa ctg cag aat     384
Pro Arg Glu Pro Arg Arg Gln Ala Thr Gln Met Leu Lys Leu Gln Asn
        115                 120                 125 ctg gtg atc ccc tgg gct cca gag aac cta aca ctt cac aaa ctg agt     432
Leu Val Ile Pro Trp Ala Pro Glu Asn Leu Thr Leu His Lys Leu Ser
    130                 135                 140 gaa tcc cag cta gaa ctg aac tgg aac aac aga ttc ttg aac cac tgt     480
Glu Ser Gln Leu Glu Leu Asn Trp Asn Asn Arg Phe Leu Asn His Cys
145                 150                 155                 160 ttg gag cac ttg gtg cag tac cgg act gac tgg gac cac agc tgg act     528
Leu Glu His Leu Val Gln Tyr Arg Thr Asp Trp Asp His Ser Trp Thr
                165                 170                 175 gaa caa tca gtg gat tat aga cat aag ttc tcc ttg cct agt gtg gat     576
Glu Gln Ser Val Asp Tyr Arg His Lys Phe Ser Leu Pro Ser Val Asp
            180                 185                 190 ggg cag aaa cgc tac acg ttt cgt gtt cgg agc cgc ttt aac cca ctc     624
Gly Gln Lys Arg Tyr Thr Phe Arg Val Arg Ser Arg Phe Asn Pro Leu
        195                 200                 205 tgt gga agt gct cag cat tgg agt gaa tgg agc cac cca atc cac tgg     672
Cys Gly Ser Ala Gln His Trp Ser Glu Trp Ser His Pro Ile His Trp
    210                 215                 220
```

```
ggg agc aat act tca aaa gag aat                                         696
Gly Ser Asn Thr Ser Lys Glu Asn
225                 230
```

<210> SEQ ID NO 4
<211> LENGTH: 232
<212> TYPE: PRT
<213> ORGANISM: Homo sapiens

<400> SEQUENCE: 4

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn
225                 230
```

<210> SEQ ID NO 5
<211> LENGTH: 654
<212> TYPE: DNA
<213> ORGANISM: Homo sapiens
<220> FEATURE:
<221> NAME/KEY: CDS
<222> LOCATION: (1)...(654)

<400> SEQUENCE: 5

```
tgc ccc gac ctc gtc tgc tac acc gat tac ctc cag acg gtc atc tgc    48
Cys Pro Asp Leu Val Cys Tyr Thr Asp Tyr Leu Gln Thr Val Ile Cys
1               5                   10                  15 atc ctg gaa atg tgg aac ctc cac ccc agc acg ctc acc ctt acc tgg    96
Ile Leu Glu Met Trp Asn Leu His Pro Ser Thr Leu Thr Leu Thr Trp
            20                  25                  30 caa gac cag tat gaa gag ctg aag gac gag gcc acc tcc tgc agc ctc   144
Gln Asp Gln Tyr Glu Glu Leu Lys Asp Glu Ala Thr Ser Cys Ser Leu
        35                  40                  45
```

```
cac agg tcg gcc cac aat gcc acg cat gcc acc tac acc tgc cac atg    192
His Arg Ser Ala His Asn Ala Thr His Ala Thr Tyr Thr Cys His Met
     50                  55                  60 gat gta ttc cac ttc atg gcc gac gac att ttc agt gtc aac atc aca    240
Asp Val Phe His Phe Met Ala Asp Asp Ile Phe Ser Val Asn Ile Thr
 65                  70                  75                  80 gac cag tct ggc aac tac tcc cag gag tgt ggc agc ttt ctc ctg gct    288
Asp Gln Ser Gly Asn Tyr Ser Gln Glu Cys Gly Ser Phe Leu Leu Ala
                 85                  90                  95 gag agc atc aag ccg gct ccc cct ttc aac gtg act gtg acc ttc tca    336
Glu Ser Ile Lys Pro Ala Pro Pro Phe Asn Val Thr Val Thr Phe Ser
            100                 105                 110 gga cag tat aat atc tcc tgg cgc tca gat tac gaa gac cct gcc ttc    384
Gly Gln Tyr Asn Ile Ser Trp Arg Ser Asp Tyr Glu Asp Pro Ala Phe
        115                 120                 125 tac atg ctg aag ggc aag ctt cag tat gag ctg cag tac agg aac cgg    432
Tyr Met Leu Lys Gly Lys Leu Gln Tyr Glu Leu Gln Tyr Arg Asn Arg
    130                 135                 140 gga gac ccc tgg gct gtg agt ccg agg aga aag ctg atc tca gtg gac    480
Gly Asp Pro Trp Ala Val Ser Pro Arg Arg Lys Leu Ile Ser Val Asp
145                 150                 155                 160 tca aga agt gtc tcc ctc ctc ccc ctg gag ttc cgc aaa gac tcg agc    528
Ser Arg Ser Val Ser Leu Leu Pro Leu Glu Phe Arg Lys Asp Ser Ser
                165                 170                 175 tat gag ctg cag gtg cgg gca ggg ccc atg cct ggc tcc tcc tac cag    576
Tyr Glu Leu Gln Val Arg Ala Gly Pro Met Pro Gly Ser Ser Tyr Gln
            180                 185                 190 ggg acc tgg agt gaa tgg agt gac ccg gtc atc ttt cag acc cag tca    624
Gly Thr Trp Ser Glu Trp Ser Asp Pro Val Ile Phe Gln Thr Gln Ser
        195                 200                 205 gag gag tta aag gaa ggc tgg aac cct cac                            654
Glu Glu Leu Lys Glu Gly Trp Asn Pro His
    210                 215

<210> SEQ ID NO 6
<211> LENGTH: 218
<212> TYPE: PRT
<213> ORGANISM: Homo sapiens

<400> SEQUENCE: 6

Cys Pro Asp Leu Val Cys Tyr Thr Asp Tyr Leu Gln Thr Val Ile Cys
 1               5                  10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
 65                  70                  75                  80

Asp Gln Ser Gly Asn Tyr Ser Gln Glu Cys Gly Ser Phe Leu Leu Ala
                 85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
        115                 120                 125

Tyr Met Leu Lys Gly Lys Leu Gln Tyr Glu Leu Gln Tyr Arg Asn Arg
    130                 135                 140
```

```
Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu Gly Trp Asn Pro His
    210                 215

<210> SEQ ID NO 7
<211> LENGTH: 1735
<212> TYPE: DNA
<213> ORGANISM: mus musculus
<220> FEATURE:
<221> NAME/KEY: CDS
<222> LOCATION: (143)...(1729)

<400> SEQUENCE: 7
ctgcccacct caaaccttca cctcccacca ccaccactcc gagtcccgct gtgactccca       60
cgcccaggag accacccaag tgccccagcc taaagaatgg ctttctgaga aagaccctga      120
aggagtaggt ctgggacaca gc atg ccc cgg ggc cca gtg gct gcc tta ctc      172
                         Met Pro Arg Gly Pro Val Ala Ala Leu Leu
                          1               5                  10 ctg ctg att ctc cat gga gct tgg agc tgc ctg gac ctc act tgc tac       220
Leu Leu Ile Leu His Gly Ala Trp Ser Cys Leu Asp Leu Thr Cys Tyr
                 15                  20                  25 act gac tac ctc tgg acc atc acc tgt gtc ctg gag aca cgg agc ccc       268
Thr Asp Tyr Leu Trp Thr Ile Thr Cys Val Leu Glu Thr Arg Ser Pro
             30                  35                  40 aac ccc agc ata ctc agt ctc acc tgg caa gat gaa tat gag gaa ctt       316
Asn Pro Ser Ile Leu Ser Leu Thr Trp Gln Asp Glu Tyr Glu Glu Leu
         45                  50                  55 cag gac caa gag acc ttc tgc agc cta cac agg tct ggc cac aac acc       364
Gln Asp Gln Glu Thr Phe Cys Ser Leu His Arg Ser Gly His Asn Thr
     60                  65                  70 aca cat ata tgg tac acg tgc cat atg cgc ttg tct caa ttc ctg tcc       412
Thr His Ile Trp Tyr Thr Cys His Met Arg Leu Ser Gln Phe Leu Ser
 75                  80                  85                  90 gat gaa gtt ttc att gtc aat gtg acg gac cag tct ggc aac aac tcc       460
Asp Glu Val Phe Ile Val Asn Val Thr Asp Gln Ser Gly Asn Asn Ser
                 95                 100                 105 caa gag tgt ggc agc ttt gtc ctg gct gag agc atc aaa cca gct ccc       508
Gln Glu Cys Gly Ser Phe Val Leu Ala Glu Ser Ile Lys Pro Ala Pro
             110                 115                 120 ccc ttg aac gtg act gtg gcc ttc tca gga cgc tat gat atc tcc tgg       556
Pro Leu Asn Val Thr Val Ala Phe Ser Gly Arg Tyr Asp Ile Ser Trp
         125                 130                 135 gac tca gct tat gac gaa ccc tcc aac tac gtg ctg agg ggc aag cta       604
Asp Ser Ala Tyr Asp Glu Pro Ser Asn Tyr Val Leu Arg Gly Lys Leu
     140                 145                 150 caa tat gag ctg cag tat cgg aac ctc aga gac ccc tat gct gtg agg       652
Gln Tyr Glu Leu Gln Tyr Arg Asn Leu Arg Asp Pro Tyr Ala Val Arg
155                 160                 165                 170 ccg gtg acc aag ctg atc tca gtg gac tca aga aac gtc tct ctt ctc       700
Pro Val Thr Lys Leu Ile Ser Val Asp Ser Arg Asn Val Ser Leu Leu
                 175                 180                 185
```

| | | |
|---|---|---|
| cct gaa gag ttc cac aaa gat tct agc tac cag ctg cag gtg cgg gca<br>Pro Glu Glu Phe His Lys Asp Ser Ser Tyr Gln Leu Gln Val Arg Ala<br>190 195 200 | 748 | |
| gcg cct cag cca ggc act tca ttc agg ggg acc tgg agt gag tgg agt<br>Ala Pro Gln Pro Gly Thr Ser Phe Arg Gly Thr Trp Ser Glu Trp Ser<br>205 210 215 | 796 | |
| gac ccc gtc atc ttt cag acc cag gct ggg gag ccc gag gca ggc tgg<br>Asp Pro Val Ile Phe Gln Thr Gln Ala Gly Glu Pro Glu Ala Gly Trp<br>220 225 230 | 844 | |
| gac cct cac atg ctg ctg ctc ctg gct gtc ttg atc att gtc ctg gtt<br>Asp Pro His Met Leu Leu Leu Leu Ala Val Leu Ile Ile Val Leu Val<br>235 240 245 250 | 892 | |
| ttc atg ggt ctg aag atc cac ctg cct tgg agg cta tgg aaa aag ata<br>Phe Met Gly Leu Lys Ile His Leu Pro Trp Arg Leu Trp Lys Lys Ile<br>255 260 265 | 940 | |
| tgg gca cca gtg ccc acc cct gag agt ttc ttc cag ccc ctg tac agg<br>Trp Ala Pro Val Pro Thr Pro Glu Ser Phe Phe Gln Pro Leu Tyr Arg<br>270 275 280 | 988 | |
| gag cac agc ggg aac ttc aag aaa tgg gtt aat acc cct ttc acg gcc<br>Glu His Ser Gly Asn Phe Lys Lys Trp Val Asn Thr Pro Phe Thr Ala<br>285 290 295 | 1036 | |
| tcc agc ata gag ttg gtg cca cag agt tcc aca aca aca tca gcc tta<br>Ser Ser Ile Glu Leu Val Pro Gln Ser Ser Thr Thr Thr Ser Ala Leu<br>300 305 310 | 1084 | |
| cat ctg tca ttg tat cca gcc aag gag aag aag ttc ccg ggg ctg ccg<br>His Leu Ser Leu Tyr Pro Ala Lys Glu Lys Lys Phe Pro Gly Leu Pro<br>315 320 325 330 | 1132 | |
| ggt ctg gaa gag caa ctg gag tgt gat gga atg tct gag cct ggt cac<br>Gly Leu Glu Glu Gln Leu Glu Cys Asp Gly Met Ser Glu Pro Gly His<br>335 340 345 | 1180 | |
| tgg tgc ata atc ccc ttg gca gct ggc caa gcg gtc tca gcc tac agt<br>Trp Cys Ile Ile Pro Leu Ala Ala Gly Gln Ala Val Ser Ala Tyr Ser<br>350 355 360 | 1228 | |
| gag gag aga gac cgg cca tat ggt ctg gtg tcc att gac aca gtg act<br>Glu Glu Arg Asp Arg Pro Tyr Gly Leu Val Ser Ile Asp Thr Val Thr<br>365 370 375 | 1276 | |
| gtg gga gat gca gag ggc ctg tgt gtc tgg ccc tgt agc tgt gag gat<br>Val Gly Asp Ala Glu Gly Leu Cys Val Trp Pro Cys Ser Cys Glu Asp<br>380 385 390 | 1324 | |
| gat ggc tat cca gcc atg aac ctg gat gct ggc cga gag tct ggc cct<br>Asp Gly Tyr Pro Ala Met Asn Leu Asp Ala Gly Arg Glu Ser Gly Pro<br>395 400 405 410 | 1372 | |
| aat tca gag gat ctg ctc ttg gtc aca gac cct gct ttt ctg tct tgc<br>Asn Ser Glu Asp Leu Leu Leu Val Thr Asp Pro Ala Phe Leu Ser Cys<br>415 420 425 | 1420 | |
| ggc tgt gtc tca ggt agt ggt ctc agg ctt gga ggc tcc cca ggc agc<br>Gly Cys Val Ser Gly Ser Gly Leu Arg Leu Gly Gly Ser Pro Gly Ser<br>430 435 440 | 1468 | |
| cta ctg gac agg ttg agg ctg tca ttt gca aag gaa ggg gac tgg aca<br>Leu Leu Asp Arg Leu Arg Leu Ser Phe Ala Lys Glu Gly Asp Trp Thr<br>445 450 455 | 1516 | |
| gca gac cca acc tgg aga act ggg tcc cca gga ggg ggc tct gag agt<br>Ala Asp Pro Thr Trp Arg Thr Gly Ser Pro Gly Gly Gly Ser Glu Ser<br>460 465 470 | 1564 | |
| gaa gca ggt tcc ccc cct ggt ctg gac atg gac aca ttt gac agt ggc<br>Glu Ala Gly Ser Pro Pro Gly Leu Asp Met Asp Thr Phe Asp Ser Gly<br>475 480 485 490 | 1612 | |
| ttt gca ggt tca gac tgt ggc agc ccc gtg gag act gat gaa gga ccc<br>Phe Ala Gly Ser Asp Cys Gly Ser Pro Val Glu Thr Asp Glu Gly Pro<br>495 500 505 | 1660 | |

```
cct cga agc tat ctc cgc cag tgg gtg gtc agg acc cct cca cct gtg    1708
Pro Arg Ser Tyr Leu Arg Gln Trp Val Val Arg Thr Pro Pro Pro Val
        510                 515                 520 gac agt gga gcc cag agc agc tagcat                                 1735
Asp Ser Gly Ala Gln Ser Ser
        525
```

<210> SEQ ID NO 8
<211> LENGTH: 529
<212> TYPE: PRT
<213> ORGANISM: mus musculus

<400> SEQUENCE: 8

```
Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Leu Gln Asp Gln Glu Thr Phe
        50                  55                  60

Cys Ser Leu His Arg Ser Gly His Asn Thr Thr His Ile Trp Tyr Thr
 65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335
```

```
Glu Cys Asp Gly Met Ser Glu Pro Gly His Trp Cys Ile Ile Pro Leu
                340                 345                 350

Ala Ala Gly Gln Ala Val Ser Ala Tyr Ser Glu Glu Arg Asp Arg Pro
            355                 360                 365

Tyr Gly Leu Val Ser Ile Asp Thr Val Thr Val Gly Asp Ala Glu Gly
        370                 375                 380

Leu Cys Val Trp Pro Cys Ser Cys Glu Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Val Asp Ser Gly Ala Gln Ser
        515                 520                 525

Ser

<210> SEQ ID NO 9
<211> LENGTH: 966
<212> TYPE: DNA
<213> ORGANISM: Homo sapiens
<220> FEATURE:
<221> NAME/KEY: CDS
<222> LOCATION: (1)...(966)

<400> SEQUENCE: 9 ggg ggc ggg ggc gcc gcg cct acg gaa act cag cca cct gtg aca aat      48
Gly Gly Gly Gly Ala Ala Pro Thr Glu Thr Gln Pro Pro Val Thr Asn
 1               5                  10                  15 ttg agt gtc tct gtt gaa aac ctc tgc aca gta ata tgg aca tgg aat      96
Leu Ser Val Ser Val Glu Asn Leu Cys Thr Val Ile Trp Thr Trp Asn
             20                  25                  30 cca ccc gag gga gcc agc tca aat tgt agt cta tgg tat ttt agt cat    144
Pro Pro Glu Gly Ala Ser Ser Asn Cys Ser Leu Trp Tyr Phe Ser His
         35                  40                  45 ttt ggc gac aaa caa gat aag aaa ata gct ccg gaa act cgt cgt tca    192
Phe Gly Asp Lys Gln Asp Lys Lys Ile Ala Pro Glu Thr Arg Arg Ser
     50                  55                  60 ata gaa gta ccc ctg aat gag agg att tgt ctg caa gtg ggg tcc cag    240
Ile Glu Val Pro Leu Asn Glu Arg Ile Cys Leu Gln Val Gly Ser Gln
 65                  70                  75                  80 tgt agc acc aat gag agt gag aag cct agc att ttg gtt gaa aaa tgc    288
Cys Ser Thr Asn Glu Ser Glu Lys Pro Ser Ile Leu Val Glu Lys Cys
                 85                  90                  95 atc tca ccc cca gaa ggt gat cct gag tct gct gtg act gag ctt caa    336
Ile Ser Pro Pro Glu Gly Asp Pro Glu Ser Ala Val Thr Glu Leu Gln
            100                 105                 110 tgc att tgg cac aac ctg agc tac atg aag tgt tct tgg ctc cct gga    384
```

```
                                                                             -continued Cys Ile Trp His Asn Leu Ser Tyr Met Lys Cys Ser Trp Leu Pro Gly
        115                 120                 125 agg aat acc agt ccc gac act aac tat act ctc tac tat tgg cac aga      432
Arg Asn Thr Ser Pro Asp Thr Asn Tyr Thr Leu Tyr Tyr Trp His Arg
130                 135                 140 agc ctg gaa aaa att cat caa tgt gaa aac atc ttt aga gaa ggc caa      480
Ser Leu Glu Lys Ile His Gln Cys Glu Asn Ile Phe Arg Glu Gly Gln
145                 150                 155                 160 tac ttt ggt tgt tcc ttt gat ctg acc aaa gtg aag gat tcc agt ttt      528
Tyr Phe Gly Cys Ser Phe Asp Leu Thr Lys Val Lys Asp Ser Ser Phe
                165                 170                 175 gaa caa cac agt gtc caa ata atg gtc aag gat aat gca gga aaa att      576
Glu Gln His Ser Val Gln Ile Met Val Lys Asp Asn Ala Gly Lys Ile
                180                 185                 190 aaa cca tcc ttc aat ata gtg cct tta act tcc cgt gtg aaa cct gat      624
Lys Pro Ser Phe Asn Ile Val Pro Leu Thr Ser Arg Val Lys Pro Asp
            195                 200                 205 cct cca cat att aaa aac ctc tcc ttc cac aat gat gac cta tat gtg      672
Pro Pro His Ile Lys Asn Leu Ser Phe His Asn Asp Asp Leu Tyr Val
        210                 215                 220 caa tgg gag aat cca cag aat ttt att agc aga tgc cta ttt tat gaa      720
Gln Trp Glu Asn Pro Gln Asn Phe Ile Ser Arg Cys Leu Phe Tyr Glu
225                 230                 235                 240 gta gaa gtc aat aac agc caa act gag aca cat aat gtt ttc tac gtc      768
Val Glu Val Asn Asn Ser Gln Thr Glu Thr His Asn Val Phe Tyr Val
                245                 250                 255 caa gag gct aaa tgt gag aat cca gaa ttt gag aga aat gtg gag aat      816
Gln Glu Ala Lys Cys Glu Asn Pro Glu Phe Glu Arg Asn Val Glu Asn
                260                 265                 270 aca tct tgt ttc atg gtc cct ggt gtt ctt cct gat act ttg aac aca      864
Thr Ser Cys Phe Met Val Pro Gly Val Leu Pro Asp Thr Leu Asn Thr
            275                 280                 285 gtc aga ata aga gtc aaa aca aat aag tta tgc tat gag gat gac aaa      912
Val Arg Ile Arg Val Lys Thr Asn Lys Leu Cys Tyr Glu Asp Asp Lys
        290                 295                 300 ctc tgg agt aat tgg agc caa gaa atg agt ata ggt aag aag cgc aat      960
Leu Trp Ser Asn Trp Ser Gln Glu Met Ser Ile Gly Lys Lys Arg Asn
305                 310                 315                 320 tcc aca                                                              966
Ser Thr <210> SEQ ID NO 10
<211> LENGTH: 322
<212> TYPE: PRT
<213> ORGANISM: Homo sapiens

<400> SEQUENCE: 10

Gly Gly Gly Gly Ala Ala Pro Thr Glu Thr Gln Pro Pro Val Thr Asn
1               5                   10                  15

Leu Ser Val Ser Val Glu Asn Leu Cys Thr Val Ile Trp Thr Trp Asn
                20                  25                  30

Pro Pro Glu Gly Ala Ser Ser Asn Cys Ser Leu Trp Tyr Phe Ser His
            35                  40                  45

Phe Gly Asp Lys Gln Asp Lys Lys Ile Ala Pro Glu Thr Arg Arg Ser
        50                  55                  60

Ile Glu Val Pro Leu Asn Glu Arg Ile Cys Leu Gln Val Gly Ser Gln
65                  70                  75                  80

Cys Ser Thr Asn Glu Ser Glu Lys Pro Ser Ile Leu Val Glu Lys Cys
                85                  90                  95
```

```
Ile Ser Pro Pro Glu Gly Asp Pro Glu Ser Ala Val Thr Glu Leu Gln
            100                 105                 110

Cys Ile Trp His Asn Leu Ser Tyr Met Lys Cys Ser Trp Leu Pro Gly
            115                 120                 125

Arg Asn Thr Ser Pro Asp Thr Asn Tyr Thr Leu Tyr Tyr Trp His Arg
            130                 135                 140

Ser Leu Glu Lys Ile His Gln Cys Glu Asn Ile Phe Arg Glu Gly Gln
145                 150                 155                 160

Tyr Phe Gly Cys Ser Phe Asp Leu Thr Lys Val Lys Asp Ser Ser Phe
                165                 170                 175

Glu Gln His Ser Val Gln Ile Met Val Lys Asp Asn Ala Gly Lys Ile
            180                 185                 190

Lys Pro Ser Phe Asn Ile Val Pro Leu Thr Ser Arg Val Lys Pro Asp
            195                 200                 205

Pro Pro His Ile Lys Asn Leu Ser Phe His Asn Asp Asp Leu Tyr Val
            210                 215                 220

Gln Trp Glu Asn Pro Gln Asn Phe Ile Ser Arg Cys Leu Phe Tyr Glu
225                 230                 235                 240

Val Glu Val Asn Asn Ser Gln Thr Glu Thr His Asn Val Phe Tyr Val
                245                 250                 255

Gln Glu Ala Lys Cys Glu Asn Pro Glu Phe Glu Arg Asn Val Glu Asn
            260                 265                 270

Thr Ser Cys Phe Met Val Pro Gly Val Leu Pro Asp Thr Leu Asn Thr
            275                 280                 285

Val Arg Ile Arg Val Lys Thr Asn Lys Leu Cys Tyr Glu Asp Asp Lys
            290                 295                 300

Leu Trp Ser Asn Trp Ser Gln Glu Met Ser Ile Gly Lys Lys Arg Asn
305                 310                 315                 320

Ser Thr
```